US012792965B2

(12) United States Patent
Chaoui et al.

(10) Patent No.: US 12,792,965 B2
(45) Date of Patent: Nov. 10, 2026

(54) COMPLEX PATIENT-MATCHED ORTHOPEDIC PROSTHESIS SELECTION

(71) Applicant: Howmedica Osteonics Corp., Mahwah, NJ (US)

(72) Inventors: Jean Chaoui, Lyons (FR); Charles L. Penninger, Warsaw, IN (US); Marine Godelu, Grenoble (FR)

(73) Assignee: Howmedica Osteonics Corp., Mahwah, NJ (US)

( * ) Notice: Subject to any disclaimer, the term of this patent is extended or adjusted under 35 U.S.C. 154(b) by 383 days.

(21) Appl. No.: 18/410,744

(22) Filed: Jan. 11, 2024

(65) Prior Publication Data

US 2024/0238096 A1 Jul. 18, 2024

Related U.S. Application Data

(60) Provisional application No. 63/479,709, filed on Jan. 12, 2023.

(51) Int. Cl.
*G06N 20/00* (2019.01)
*A61F 2/30* (2006.01)
(Continued)

(52) U.S. Cl.
CPC ......... *G06N 20/00* (2019.01); *A61F 2/30942* (2013.01); *G06N 3/0455* (2023.01);
(Continued)

(58) Field of Classification Search
CPC .. G06N 20/00; G06N 3/0455; A61F 2/30942; A61F 2002/30943
(Continued)

(56) References Cited

U.S. PATENT DOCUMENTS 8,160,325 B2 4/2012 Zug et al.
8,231,634 B2 7/2012 Mahfouz et al.
(Continued)

FOREIGN PATENT DOCUMENTS

EP 3921837 A1 12/2021
WO 2020163358 A1 8/2020
(Continued)

OTHER PUBLICATIONS

Banga et al., “3D Topology Optimization Using Convolutional Neural Networks,” Carnegie Mellon University, Aug. 2018, 21 pp.
(Continued)

*Primary Examiner* — Jeffery A Williams
(74) *Attorney, Agent, or Firm* — Shumaker & Sieffert, P.A.

(57) ABSTRACT

A method comprises generating initial designs that represent an orthopedic prosthesis customized for a patient; generating alternative designs based on the initial designs, wherein the alternative designs represent the orthopedic prosthesis and generating the alterative designs comprises, for each initial design in the set of initial designs: applying an encoder model that generates a vector based on the initial design, wherein the encoder model is part of an autoencoder; generating a set of modified vectors by modifying one or more elements of the vector; applying a decoder model to the modified vectors to generate one or more of the alternative designs, wherein the decoder model is part of the autoencoder, and the alternative designs represent the orthopedic prosthesis; and selecting a design for the orthopedic prosthesis based from the initial designs or the alternative designs.

20 Claims, 13 Drawing Sheets

(51) Int. Cl.
*G06N 3/0455* (2023.01)
*G06T 7/00* (2017.01)

(52) U.S. Cl.
CPC ...... *G06T 7/00* (2013.01); *A61F 2002/30943* (2013.01); *G06T 2207/20081* (2013.01); *G06T 2207/20092* (2013.01)

(58) Field of Classification Search
USPC ............................................................ 706/16
See application file for complete search history.

(56) References Cited

U.S. PATENT DOCUMENTS

| | | | |
|---|---|---|---|
| 8,532,807 | B2 | 9/2013 | Metzger |
| 8,634,618 | B2 | 1/2014 | Zug et al. |
| 8,903,530 | B2 | 12/2014 | Metzger |
| 9,504,579 | B2 | 11/2016 | Mahfouz et al. |
| 9,649,170 | B2 | 5/2017 | Park et al. |
| 9,757,238 | B2 | 9/2017 | Metzger |
| 9,814,533 | B2 | 11/2017 | Park et al. |
| 10,159,513 | B2 | 12/2018 | Pavlovskaia et al. |
| 10,182,870 | B2 | 1/2019 | Park et al. |
| 10,262,084 | B2 | 4/2019 | Lavallee et al. |
| 10,667,867 | B2 | 6/2020 | Gangwar et al. |
| 10,675,063 | B2 | 6/2020 | Pavlovskaia et al. |
| 10,762,623 | B2 | 9/2020 | Geebelen et al. |
| 10,973,535 | B2 | 4/2021 | Iannotti et al. |
| 11,263,772 | B2 | 3/2022 | Siemionow et al. |
| 11,278,413 | B1 | 3/2022 | Lang |
| 11,344,370 | B2 | 5/2022 | Park et al. |
| 11,410,769 | B1 | 8/2022 | Yildirim |
| 11,432,931 | B2 | 9/2022 | Lang |
| 11,443,846 | B2 | 9/2022 | Schoenefeld et al. |
| 11,490,966 | B2 | 11/2022 | Roche et al. |
| 11,621,086 | B2 | 4/2023 | Spanberg et al. |
| 11,653,976 | B2 | 5/2023 | Bonny et al. |
| 11,660,197 | B1 | 5/2023 | Lang |
| 11,717,412 | B2 | 8/2023 | Casey et al. |
| 11,751,946 | B2 | 9/2023 | Gangwar et al. |
| 11,847,755 | B2 | 12/2023 | Park et al. |
| 2009/0089034 | A1 | 4/2009 | Penney et al. |
| 2014/0303938 | A1 | 10/2014 | Schoenfeld et al. |
| 2014/0303990 | A1 | 10/2014 | Schoenefeld et al. |
| 2017/0035513 | A1 | 2/2017 | Mahfouz et al. |
| 2021/0322130 | A1 | 10/2021 | Penney et al. |
| 2021/0391058 | A1 | 12/2021 | Kostrzewski et al. |
| 2022/0125515 | A1 | 4/2022 | McGuan et al. |
| 2022/0156924 | A1 | 5/2022 | Poltaretskyi et al. |
| 2022/0233159 | A1 | 7/2022 | Yoon et al. |
| 2022/0346968 | A1 | 11/2022 | Pettersson et al. |
| 2022/0351410 | A1 | 11/2022 | Siemionow et al. |
| 2022/0351828 | A1 | 11/2022 | Chaoui |
| 2022/0370142 | A1 | 11/2022 | Schoenefeld et al. |
| 2022/0387110 | A1 | 12/2022 | Chaoui |
| 2023/0139531 | A1 | 5/2023 | Roche et al. |
| 2023/0248435 | A1 | 8/2023 | Bonny et al. |
| 2023/0317298 | A1 | 10/2023 | Spanberg et al. |
| 2023/0372018 | A1 | 11/2023 | Gangwar et al. |
| 2024/0156578 | A1 * | 5/2024 | Ahn .................. A61C 13/0004 |

FOREIGN PATENT DOCUMENTS

| | | | |
|---|---|---|---|
| WO | 2022150437 | A1 | 7/2022 |
| WO | 2022183719 | A1 | 9/2022 |

OTHER PUBLICATIONS

Burnap et al., "Estimating and Exploring the Product Form Design Space Using Deep Generative Models," Proceedings of the ASME 2016 International Design Engineering Technical Conferences and Computers and Information in Engineering Conference IDETC/CIE 2016, Aug. 21-24, 2016, 13 pp.

Feng et al., "MeshNet: Mesh Neural Network for 3D Shape Representation," The Thirty-Third AAAI Conference on Artificial Intelligence (AAAI-19), Jan. 2019, pp. 8279-8286.

Guo et al., "An Indirect Design Representation for Topology Optimization Using Variational Autoencoder and Style Transfer," 2018 AIAA/ASCE/AHS/ASC Structures, Structural Dynamics, and Materials Conference, Jan. 2018, 22 pp.

Kanezaki et al., "RotationNet: Joint Object Categorization and Pose Estimation Using Multiviews from Unsupervised Viewpoints," 2018 IEEE/CVF Conference on Computer Vision and Pattern Recognition, Jun. 18-23, 2018, pp. 5010-5019.

Maturana et al., "VoxNet: A 3D Convolutional Neural Network for Real-Time Object Recognition," 2015 IEEE/RSJ International Conference on Intelligent Robots and Systems (IROS), Sep. 28, 2015-Oct. 2, 2015, 7 pp.

Oh et al., "Deep Generative Design: Integration of Topology Optimization and Generative Models," Journal of Mechanical Design, vol. 141, No. 11, Jul. 2019, 22 pp.

Qi et al., "PointNet: Deep Learning on Point Sets for 3D Classification and Segmentation," 2017 IEEE Conference on Computer Vision and Pattern Recognition (CVPR), Jul. 21-26, 2017, pp. 652-660.

Su et al., "Multi-view Convolutional Neural Networks for 3D Shape Recognition," 2015 IEEE International Conference on Computer Vision (ICCV), May 2015, pp. 945-953.

Umetani, "Exploring Generative 3D Shapes Using Autoencoder Networks," SIGGRAPH Asia Technical Brief, Nov. 2017, 4 pp.

Yu et al., "Deep Learning for Determining a Near-Optimal Topological Design without any Iteration," Structural and Multidisciplinary Optimization, Mar. 2019, 27 pp.

* cited by examiner

COMPLEX PATIENT-MATCHED ORTHOPEDIC PROSTHESIS SELECTION

This application claims the benefit of U.S. Provisional Patent Application 63/479,709, filed Jan. 12, 2023, the entire content of which is incorporated by reference.

BACKGROUND

Orthopedic surgeries are often very complex, and consequently may require detailed planning. For example, when performing a total shoulder arthroplasty, a surgeon may need to carefully select appropriate orthopedic prostheses and plan how the selected orthopedic prostheses are to be positioned. When planning an orthopedic surgery, a typical goal is to restore the ability of a patient to move at a joint in the same manner as the patient did prior to the onset of a pathology affecting the joint.

SUMMARY

This disclosure describes example techniques for planning complex patient-matched orthopedic prostheses. As described herein, a computing system may use machine learning (ML) models at various points in a process of selecting orthopedic prosthesis designs that are customized to an individual patient. For example, the computing system may apply one or more ML models to recommend that the patient receive an orthopedic prosthesis that is customized to the patient. In some examples, the computing system may apply one or more ML models to generate and select 2-dimensional or 3-dimensional designs for orthopedic prostheses.

In one example, this disclosure describes a method comprising: generating, by a computing system, a set of one or more initial designs that represents an orthopedic prosthesis customized for a patient; generating, by the computing system, one or more alternative designs based on the set of initial designs, wherein the one or more alternative designs represent the orthopedic prosthesis customized for the patient and wherein generating the one or more alterative designs comprises, for each initial design in the set of initial designs: applying, by the computing system, an encoder model that generates a latent space vector based on the initial design, wherein the encoder model is a first machine learning (ML) model, the encoder model is part of an autoencoder, and the latent space vector has reduced dimensionality relative to the initial design; generating, by the computing system, a set of one or more modified latent space vectors by modifying one or more elements of the latent space vector; applying, by the computing system, a decoder model to the one or more modified latent space vectors to generate one or more of the alternative designs, wherein the decoder model is a second ML model, the decoder model is part of the autoencoder, and the alternative designs represent the orthopedic prosthesis; and selecting, by the computing system, a design for the orthopedic prosthesis from the initial designs or the set of alternative designs.

In another example, this disclosure describes a computing system comprising: a storage system; and processing circuitry configured to generate a set of one or more initial designs that represents an orthopedic prosthesis customized for a patient; generate one or more alternative designs based on the set of initial designs, wherein the one or more alternative designs represent the orthopedic prosthesis customized for the patient, and wherein processing circuitry is configured to, as part of generating the one or more alternative designs, for each initial design in the set of initial designs: apply an encoder model that generates a latent space vector based on the initial design, wherein the encoder model is a first machine learning (ML) model, the encoder model is part of an autoencoder, and the latent space vector has reduced dimensionality relative to the initial design; generate a set of one or more modified latent space vectors by modifying one or more elements of the latent space vector; apply a decoder model to the one or more modified latent space vectors to generate one or more of the alternative designs, wherein the decoder model is a second ML model, the decoder model is part of the autoencoder; and select a design for the orthopedic prosthesis from the initial designs or the set of alternative designs.

In another example, this disclosure describes a non-transitory computer readable storage medium having instructions stored thereon that, when executed, cause a computing system to generate a set of one or more initial designs that represents an orthopedic prosthesis customized for a patient; generate one or more alternative designs based on the set of initial designs, wherein the one or more alternative designs represent the orthopedic prosthesis customized for the patient, and wherein processing circuitry is configured to, as part of generating the one or more alternative designs, for each initial design in the set of initial designs: apply an encoder model that generates a latent space vector based on the initial design, wherein the encoder model is a first machine learning (ML) model, the encoder model is part of an autoencoder, and the latent space vector has reduced dimensionality relative to the initial design; generate a set of one or more modified latent space vectors by modifying one or more elements of the latent space vector; apply a decoder model to the one or more modified latent space vectors to generate one or more of the alternative designs, wherein the decoder model is a second ML model, the decoder model is part of the autoencoder; and select a design for the orthopedic prosthesis from the initial designs or the set of alternative designs.

The details of various examples of the disclosure are set forth in the accompanying drawings and the description below. Various features, objects, and advantages will be apparent from the description, drawings, and claims.

DETAILED DESCRIPTION

Figure 1:
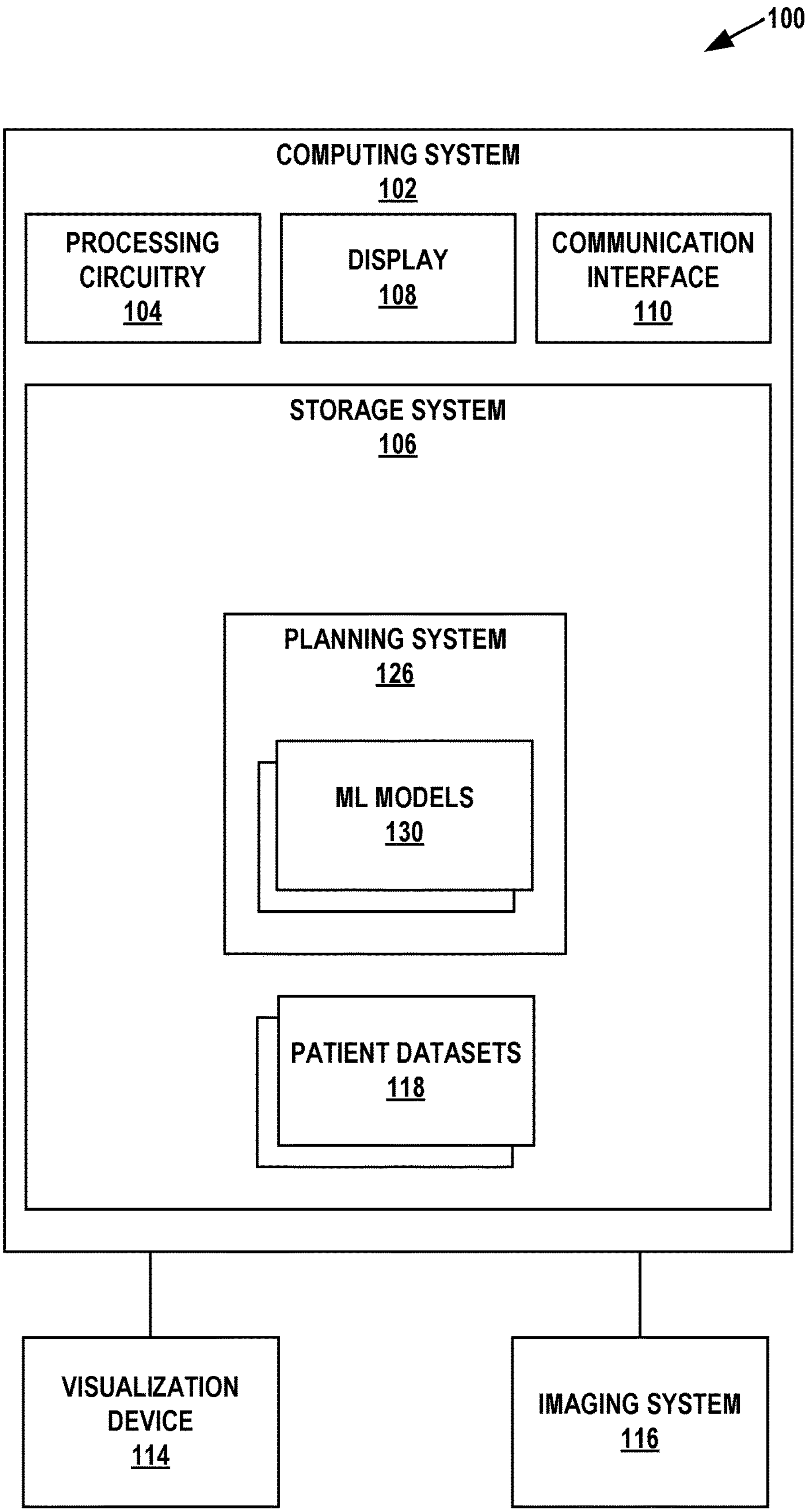
FIG. 1 is a block diagram illustrating an example system that may be used to implement the techniques of this disclosure.

Total shoulder arthroplasty is a type of orthopedic surgery in which orthopedic prostheses are implanted into a patient's scapula and humerus. The orthopedic prostheses provide articulating surfaces to allow smooth movement of the patient's arm. In some instances, the patient's scapula is severely deformed, e.g., due to bone loss or trauma. In cases where the patient's scapula is severely deformed, a surgeon may be unable to attach conventional glenoid prostheses to the patient's scapula. Moreover, in cases where the patient's scapula is severely deformed, it may be difficult for a surgeon to plan a total shoulder arthroplasty because it may be difficult for the surgeon to determine an appropriate position of the glenoid prosthesis.

This disclosure describes computer-implemented planning systems for complex patient-matched orthopedic prostheses, such as patient-matched glenoid prostheses. As set forth herein, a computing system may use machine learning (ML) models at various points in a process of orthopedic prosthesis selection that are customized to an individual patient. For example, the computing system may apply one or more ML models to recommend that the patient receive an orthopedic prosthesis that is customized to the patient. In some examples, the computing system may apply one or more ML models to generate and select 2-dimensional or 3-dimensional designs for orthopedic prostheses.

One challenge associated with cases where the patient has severe bone deformity is that an orthopedic prosthesis suitable for the patient may occupy considerably more area than orthopedic prostheses for more typical amounts of bone deformity. Accordingly, a process of selecting a shape of an orthopedic prosthesis suitable for a patient with severe bone deformity is not easily characterized by a small number of parameters characterizing the patient's bone. This disclosure describes techniques that enable a computing system to automatically generate and select designs for orthopedic prostheses. For instance, in some examples, the computing system may generate a set of one or more initial designs that represents an orthopedic prosthesis customized for a patient. The computing system may also generate one or more alternative designs based on the set of initial designs. The one or more alternative designs represent the orthopedic prosthesis customized for the patient. As part of generating the one or more alterative designs, the computing system may, for each initial design in the set of initial designs, apply an encoder model that generates a latent space vector based on the initial design. The encoder model is a first machine learning (ML) model and is part an autoencoder. The latent space vector has reduced dimensionality relative to the initial design. Additionally, as part of generating the alternative designs, the computing system may generate a set of one or more modified latent space vectors by modifying one or more elements of the latent space vector. Furthermore, as part of generating the alternative designs, the computing system may apply a decoder model to the one or more modified latent space vectors to generate one or more of the alternative designs. The decoder model may be a second ML model and may be part of the autoencoder. The alternative designs represent the orthopedic prosthesis. The computing system may select a design for the orthopedic prosthesis from the initial design or the set of alternative designs.

FIG. 1 is a block diagram illustrating an example system 100 that may be used to implement the techniques of this disclosure. In the example of FIG. 1, system 100 includes a computing system 102. Computing system 102 is an example of one or more computing devices that are configured to perform one or more example techniques described in this disclosure. Computing system 102 may include various types of computing devices, such as server computers, personal computers, smartphones, laptop computers, and other types of computing devices. In some examples, computing system 102 includes multiple computing devices that communicate with each other. In other examples, computing system 102 includes only a single computing device. Computing system 102 includes processing circuitry 104, a storage system 106, a display 108, and a communication interface 110. Display 108 may be optional, such as in examples where computing system 102 is a server computer.

Examples of processing circuitry 104 include one or more microprocessors, digital signal processors (DSPs), application specific integrated circuits (ASICs), field programmable gate arrays (FPGAs), discrete logic, software, hardware, firmware or any combinations thereof. Processing circuitry 104 may be implemented as fixed-function circuits, programmable circuits, or a combination thereof. Fixed-function circuits refer to circuits that provide particular functionality and are preset on the operations that can be performed. Programmable circuits refer to circuits that can be programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. In some examples, processing circuitry 104 is dispersed among a plurality of computing devices in computing system 102. In some examples, processing circuitry 104 is contained within a single computing device of computing system 102. Processing circuitry 104 may include arithmetic logic units (ALUs), elementary function units (EFUs), digital circuits, analog circuits, and/or programmable cores, formed from programmable circuits. In examples where the operations of processing circuitry 104 are performed using software executed by the programmable circuits, storage system 106 may store the object code of the software that processing circuitry 104 receives and executes, or another memory within processing circuitry 104 (not shown) may store such instructions. Examples of the software include software designed for surgical planning.

Storage system 106 may be formed by any of a variety of memory devices, such as dynamic random access memory (DRAM), including synchronous DRAM (SDRAM), magnetoresistive RAM (MRAM), resistive RAM (RRAM), or other types of memory devices. Examples of display 108 include a liquid crystal display (LCD), a plasma display, an organic light emitting diode (OLED) display, or another type of display device. In some examples, storage system 106 may include multiple separate memory devices, such as multiple disk drives, memory modules, etc., that may be dispersed among multiple computing devices or contained within the same computing device.

Communication interface 110 may include hardware circuitry that enables computing system 102 to communicate (e.g., wirelessly or using wires) to other computing systems and devices, such as a visualization device 114 and an imaging system 116. In some examples, communication interface 110 may communicate with other computing systems and devices via a network, which may include various types of communication networks including one or more wide-area networks, such as the Internet, local area networks, and so on. In some examples, the network may include wired and/or wireless communication links.

Visualization device 114 may utilize various visualization techniques to display image content to a surgeon. In some examples, visualization device 114 is a computer monitor or display screen. In some examples, visualization device 114 may be a mixed reality (MR) visualization device, virtual reality (VR) visualization device, holographic projector, or other device for presenting extended reality (XR) visualizations. For instance, in some examples, visualization device 114 may be a Microsoft HOLOLENS™ headset, available from Microsoft Corporation, of Redmond, Washington, USA, or a similar device, such as, for example, a similar MR visualization device that includes waveguides. The HOLOLENS™ device can be used to present 3D virtual objects via holographic lenses, or waveguides, while permitting a user to view actual objects in a real-world scene, i.e., in a real-world environment, through the holographic lenses. In some examples, there may be multiple visualization devices for multiple users.

Visualization device 114 may utilize visualization tools that are available to utilize patient image data to generate three-dimensional models of bones, segmentation masks, or other data to facilitate preoperative planning. These tools may allow surgeons to design and/or select surgical guides and implant components that closely match the patient's anatomy. These tools can improve surgical outcomes by customizing a surgical plan for each patient. An example of such a visualization tool is the BLUEPRINT™ system available from Stryker Corp. The surgeon can use the BLUEPRINT™ system to select, design or modify appropriate implant components, determine how best to position and orient the implant components and how to shape the surface of the bone to receive the components, and design, select or modify surgical guide tool(s) or instruments to carry out the surgical plan. The information generated by the BLUEPRINT™ system may be compiled in a preoperative surgical plan for the patient that is stored in a database at an appropriate location, such as storage system 106, where the preoperative surgical plan can be accessed by the surgeon or other care provider, including before and during the actual surgery.

Imaging system 116 may comprise one or more devices configured to generate medical image data. For example, imaging system 116 may include a device for generating CT images. In some examples, imaging system 116 may include a device for generating MRI images. Furthermore, in some examples, imaging system 116 may include one or more computing devices configured to process data from imaging devices in order to generate medical image data. For example, the medical image data may include a 3D image of one or more bones of a patient. In this example, imaging system 116 may include one or more computing devices configured to generate the 3D image based on CT images or MRI images. In some examples, the medical image data may include a point cloud representing one or more bones of a patient. In this example, imaging system 116 may include one or more computing devices configured to generate the point cloud. Each point in the point cloud may correspond to a set of 3D coordinates of a point on a surface of a bone of the patient. Imaging system 116 may generate the point cloud by identifying the surfaces of the one or more bones in images and sampling points on the identified surfaces. In other examples, computing system 102 may include one or more computing devices configured to generate the medical image data based on data from devices in imaging system 116.

Storage system 106 of computing system 102 may store instructions that, when executed by processing circuitry 104, cause computing system 102 to perform various activities. For instance, in the example of FIG. 1, storage system 106 may store instructions that, when executed by processing circuitry 104, cause computing system 102 to perform activities associated with a planning system 126. For case of explanation, rather than discussing computing system 102 performing activities when processing circuitry 104 executes instructions, this disclosure may simply refer to planning system 126 or components thereof as performing the activities, or may directly describe computing system 102 as performing the activities.

In the example of FIG. 1, storage system 106 includes one or more patient datasets 118. Each of patient datasets 118 may include data associated with a patient. The data associated with a patient may include demographic information of the patient, a diagnosis of the patient, a surgical plan for the patient, and other types of information of the patient. Additionally, the data associated with a patient may include bone models for the patient. The bone models for a patient may include a morbid bone model. The morbid bone model may be a bone model representing a current (morbid) state of a bone of the patient. Computing system 102 may obtain morbid bone model based on medical imaging data generated by imaging system 116. In this disclosure, the term "bone" may refer to a whole bone or a bone fragment. In some examples, storage system 106 does not include patient datasets 118.

Planning system 126 may help a user plan an orthopedic surgery. For example, planning system 126 may help a user plan an orthopedic surgery that involves attaching a glenoid prosthesis to a scapula of a patient. In this example, planning system 126 may recommend a glenoid prosthesis for the patient based on data in a patient dataset for the patient. Planning system 126 may apply one or more machine-learned (ML) models 130 as part of a process to recommend the glenoid prosthesis for the patient. In different examples of this disclosure, planning system 126 may receive different types of input from the user, may apply different types and numbers of ML models to recommend the glenoid prosthesis for the patient. In some examples, planning system 126 may output a 3D image of the recommended glenoid prosthesis for display, e.g., on display 108, visualization device 114, or another device. In some examples, planning system 126 may help a user plan one or more aspects of a glenoid prosthesis, such as the size or shape of a base plate of the glenoid prosthesis, or placement of fixation holes in the glenoid prosthesis.

Figure 2:
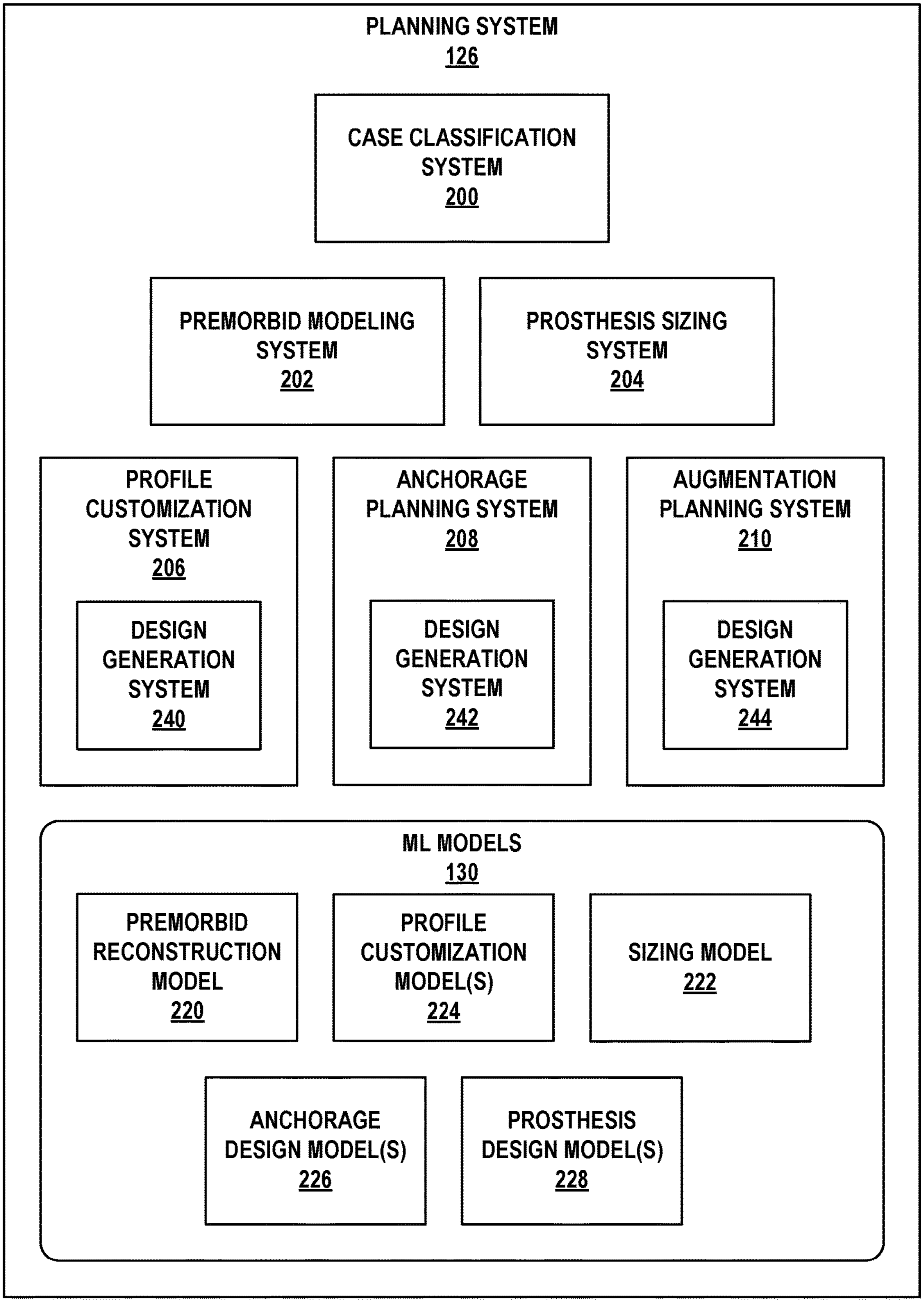
FIG. 2 is a block diagram illustrating an example planning system according to techniques of this disclosure.

FIG. 2 is a block diagram illustrating an example planning system 126 according to techniques of this disclosure. In the example of FIG. 2, planning system 126 includes a case classification system 200, a premorbid modeling system 202, a prosthesis sizing system 204, a profile customization system 206, an anchorage planning system 208, and an augmentation planning system 210. Furthermore, in the example of FIG. 2, ML models 130 includes a premorbid reconstruction model 220, a sizing model 222, one or more profile customization models 224, one or more anchorage design models 226, and one or more prosthesis design models 228. In other examples, planning system 126 may include more or fewer systems and ML models. For example, prosthesis sizing system 204 may be omitted from planning system 126.

Case classification system 200 may apply one or more of ML models 130 to identify a case classification for a patient. Different case classifications may correspond to different types of glenoid prostheses. Example types of glenoid prostheses may include patient-specific implants (PSI), patient-matched implants (PMIs), complex patient-matched implants, custom implants, patient-tailored implants, and so on. A custom implant is an implant that is fully designed to match 100% of the patient anatomy, that covers cases where the morbidity level is very high like in the cases of tumor removal or severe trauma with severe bone loss. A patient-matched implant is an implant where only one or few components match the patient anatomy (low deformity, low bone limited bone loss). A complex patient-matched implant is a patient-matched implant where the patient anatomy involves high deformity or bone loss or dysplasia (mid to high bone loss). A patient-tailored implant is an implant that has a geometry that approximates the patient anatomy but is selected from among a plurality of standardized shapes and sizes. Example details of case classification system 200 are discussed in greater detail elsewhere in this disclosure, e.g., with respect to FIG. 6.

When the patient has severe bone loss, restoring appropriate lateralization of the shoulder joint is important for restoring the patient's range of motion and proper joint biomechanics. Lateralization of the shoulder joint refers to the distance from a midline of the patient to an articulating surface of the shoulder joint. When the patient has severe bone loss, the lateralization of the shoulder joint may be reduced. Restoring the patient's range of motion and proper biomechanics may require implantation of a glenoid prosthesis that restores the articulating surface of the shoulder to the proper lateralization. However, when presented with a 2D or 3D models of the patient's scapula, it may be difficult for a surgeon to determine the proper lateralization of the patient's shoulder joint. For instance, the surgeon may typically rely on landmarks such as the anterior rim or posterior rim of the patient's glenoid fossa to determine the proper lateralization of the patient's shoulder joint. When the patient has severe bone loss, such landmarks may be absent.

Hence, in accordance with techniques of this disclosure, premorbid modeling system 202 may apply premorbid reconstruction model 220 to generate a premorbid bone model. The premorbid bone model may include one or more 2D images or a 3D model of a patient's scapula (or other bone) prior to onset of a morbidity, such as bone loss or trauma. The premorbid bone model may be used (e.g., by planning system 126 or a clinician) as a basis for generating a glenoid prosthesis model. For example, planning system 126 or the clinician may use the premorbid bone model to identify a reference plane of the premorbid bone model. The reference plane of the premorbid bone model is a line that connects the lateral-most points on the glenoid rim of the premorbid bone model. The reference plane of the premorbid bone model may therefore correspond to an appropriate lateralization of the shoulder joint.

In some examples, premorbid reconstruction model 220 is based on a statistical shape model (SSM). The SSM may be based on a library of premorbid scapulae. In essence, the SSM returns information indicating a most probable shape of the patient's premorbid scapula given the positions of landmarks on the patient's current scapula. U.S. Patent Publication 2022/0156924, published May 19, 2022, the entire content of which is incorporated by reference, describes an example process for generating a premorbid bone model based on an SSM. In accordance with examples described in U.S. Patent Publication 2022/0156924, premorbid reconstruction model 220 may represent anatomy shape variations by adding points or values of a premorbid model to a covariance matrix. For example, the SSM can be interpreted as a linear equation:

$$s_i = s' + \Sigma_i b_i \sqrt{\lambda_i} \times v_i \quad (1)$$

In equation (1), above, s' is the premorbid bone model (e.g., point cloud of mean shape as one example, where point cloud defines coordinates of points within the premorbid bone model, such as vertices of primitives that form the premorbid bone model). In the equation above, $\lambda_i$ is the eigenvalues and $v_i$ is the eigenvectors of the covariance matrix respectively (also called modes of variations). The covariance matrix represents the variance in a dataset. The element in the i, j position is the co-variance between the i-th and j-th elements of a dataset array.

SSM stands for constructing the covariance matrix of the database then performing "singular value decomposition" which extracts a matrix of principal vectors (also called eigenvectors) and another diagonal matrix of positive values (called eigenvalues). Eigenvectors ($v_i$ in equation 1)) are new coordinate system bases of the database. Eigenvalues ($\lambda_i$ in equation (1)) represent the variance around the eigenvectors ($v_i$). Together eigenvectors and eigenvalues may reflect the amount of variation around the corresponding axis.

Equation (1) may allow premorbid modeling system 202 to create many instances of $s_j$ (e.g., different variations of the shape model) by simply changing the weights $b_i$ of the covariance matrix. For instance, to generate a new shape model, premorbid modeling system 202 may determine a value of $b_i$, and determine a new value of $s_i$. In the above example, $\lambda_i$ and $v_i$ and s' are all known based on the manner in which s' was generated (e.g., based on the manner in which the premorbid bone model was generated). By selecting different values of $b_i$, premorbid modeling system 202 may determine different instances of a shape model (e.g., different $s_i$ which are different variations of the premorbid bone model).

The shape model(s) may represent what an anatomical object should look like for a patient. Premorbid modeling system 202 may compare points (e.g., in the 3D cloud of points) of the shape model of the anatomical object with anatomical points represented in the image data of scans of the patient's bones, as anatomical points of the anatomical object that are not impacted or minimally impacted by the injury or disease (e.g., non-pathological points). Based on the comparison, premorbid modeling system 202 may determine a pre-morbid characterization of the anatomical object.

As an example, assume that the clinician would like to determine the pre-morbid characteristics of the glenoid cavity for shoulder surgery. There is a correlation between the shape of the glenoid cavity and the bony zone around it, such as the medical glenoid vault, the acromion, and the coracoid. The premorbid bone model may be the mean shape of the scapula that includes the glenoid cavity. Assume that in the patient the glenoid cavity is pathological (e.g., diseased or damaged). In accordance with example techniques described in this disclosure, premorbid modeling system 202 may determine the instance of "s" (e.g., shape model of scapula with glenoid cavity) that best matches the non-pathological anatomy of the anatomical object of the patient (e.g., non-pathological portions of the scapula in scans of the scapula). The glenoid cavity, in the instance of "s," that best matches the non-pathological anatomy (referred to as s* and represented by a point cloud similar to the shape model) may be indicative of the pre-morbid characterization of the pathological glenoid cavity.

Premorbid modeling system 202 may determine the instance of s* (e.g., premorbid bone model of scapula with glenoid cavity that best matches the non-pathological portions of the patient's scapula). The non-pathological portions may be portions of the anatomical object with minimal to no impact from the disease or injury, where the anatomical object and its surrounding anatomy are taken from the segmentation performed by the scans of the bone to segment out the anatomical object.

In some examples, premorbid modeling system 202 may identify the reference plane of the premorbid bone model. The clinician may review the identified reference plane. Premorbid modeling system 202 may receive indications of user input from the clinician to adjust the reference plane. In some examples, premorbid modeling system 202 and/or the clinician may analyze the premorbid bone model to identify other parameters of the glenoid articulating surface, such as retroversion, inclination, center of rotation, and so on. Premorbid modeling system 202 may provide a user interface to receive indications of user input to adjust one or more of these parameters. In an example where premorbid modeling system 202 identifies the reference plane, premorbid modeling system 202 may identify the reference plane by identifying the most superior point, most inferior point, most anterior point, and most posterior point on a glenoid rim of the premorbid bone model. Premorbid modeling system 202 may determine the reference plane as a plane that fits these four points.

In some examples, premorbid modeling system 202 may also determine a center of rotation of the patient's shoulder based on the premorbid bone model. For example, premorbid modeling system 202 may fit a sphere (or spheroid) to the glenoid fossa in the premorbid bone model. Premorbid modeling system 202 may determine that the center of the fitted sphere (or spheroid) is the center of rotation of the patient's shoulder. Premorbid modeling system 202 may determine a version of a glenoid prosthesis as an angle between a frontal plane passing through a point at a center of curvature of the glenoid fossa of the premorbid bone model and a line from the point to the center of the sphere (or spheroid) projected onto a transverse plane. Premorbid modeling system 202 may determine an inclination of the glenoid prosthesis as an angle between a transverse plane passing through the point at the center of curvature of the glenoid fossa of the premorbid bone model and a line from the point to the center of the sphere projected onto the frontal plane. In some examples, premorbid modeling system 202 may determine the reference plane based on the determined version and inclination. For instance, premorbid modeling system 202 may determine the reference plane as a plane having the determined version and inclination angles at a specific lateralization distance.

The reference plane of the premorbid bone model may correspond to a medial side of a baseplate of a glenoid prosthesis. The glenoid prosthesis may be attached to the patient's scapula by passing fixation elements, such as screws, through holes in the baseplate and into the patient's scapula. In cases where the patient does not have severe bone loss, width and height dimensions of the baseplate are similar to width and height dimensions of the patient's glenoid fossa. However, when the patient has severe bone loss, there may not be sufficient bone area in or medial to the patient's glenoid fossa to securely attach the baseplate to the scapula. Accordingly, parts of the scapula outside the glenoid fossa may be used as points to attach the baseplate to the scapula. For instance, the baseplate may have a fixation hole through which a fixation element may be passed into an acromion process or coracoid process of the scapula. However, using parts of the scapula outside the glenoid fossa as attachment points may increase the bulk of the glenoid prosthesis, which may increase costs, alter the patient's biomechanics, or have other consequences. Therefore, it may be desirable to minimize the size of the glenoid prosthesis in the reference plane while still ensuring that the glenoid prosthesis can be securely attached to the scapula.

Figure 3:
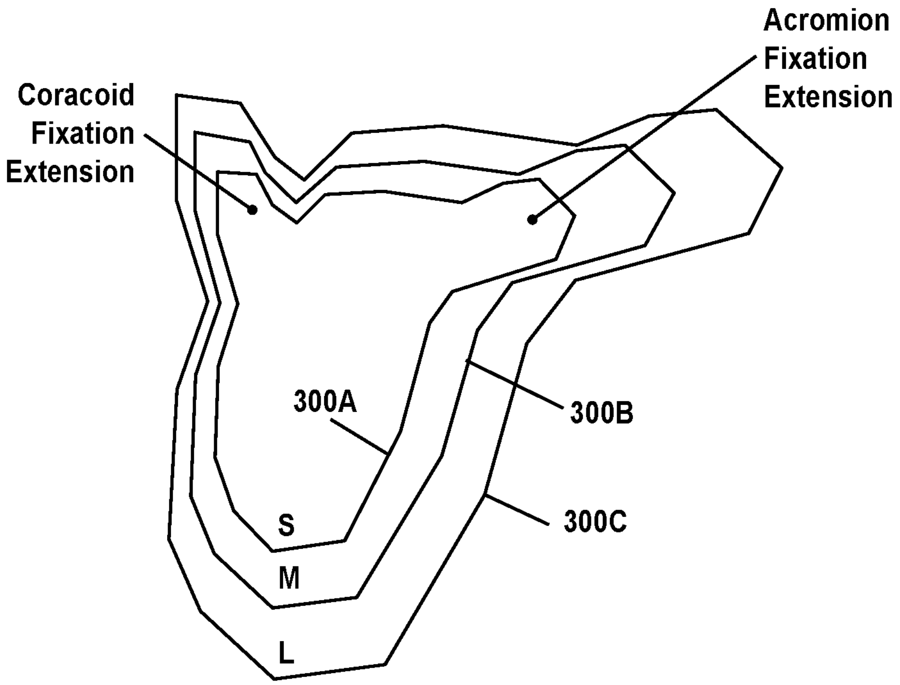
FIG. 3 is a conceptual diagram illustrating outlines of three example glenoid prosthesis baseplates having different sizes according to techniques of this disclosure.

Hence, in some examples, prosthesis sizing system 204 of planning system 126 may provide a user interface by which the surgeon can select a size of the glenoid prosthesis in the reference plane. Thus, prosthesis sizing system 204 may receive an indication of user input to select a size of the glenoid prosthesis in the reference plane. FIG. 3 is a conceptual diagram illustrating outlines of three example glenoid prosthesis baseplate elements 300A, 300B, 300C having different sizes according to techniques of this disclosure. Each of the three glenoid prosthesis baseplate elements have extensions for attaching the glenoid prosthesis baseplates to the patient's coracoid and acromion processes.

In some examples, prosthesis sizing system 204 may apply sizing model 222 to identify a recommended size of the baseplate element from among a plurality of predetermined sizes. Sizing model 222 may be an ML model trained to identify a recommended size of the glenoid prosthesis. For example, sizing model 222 may be a deep learning model, such as a convolutional neural network. Inputs to sizing model 222 may include a bone model representing at least a portion of the patient's scapula. The bone model may be formatted in one of a variety of ways. For instance, the bone model may be formatted as a voxel grid, a point cloud, multiple 2-dimensional views, a mesh, or another format. Accordingly, sizing model 222 may be implemented based on any of the voxel-based ML classification models (e.g., Maturana et al., "VoxNet: A 3D Convolutional Neural Network for Real-Time Object Recognition."), point cloud-based ML classification models (e.g., Qi et al., "PointNet: Deep Learning on Point Sets for 3D Classification and Segmentation"), 2-dimensional multiview-based ML classification models (e.g., Su et al., "Multi-view Convolutional Neural Networks for 3D Shape Recognition" or Kanezaki et al., "RotationNet: Joint Object Categorization and Pose Estimation Using Multiviews from Unsupervised Viewpoints"), or mesh-based ML classification models (e.g., Feng et al., "MeshNet: Mesh Neural Network for 3D Shape Representation"). In some examples, the inputs to sizing model 222 include data representing the reference plane. In some examples, the inputs to sizing model 222 may include additional patient data. For instance, the inputs to sizing model 222 may include data regarding one or more of patient age, sex, activities, and so on.

In some examples, rather than prosthesis sizing system 204 identifying a recommended size of the baseplate element, design generation system 240 of profile customization system 206 may generate a baseplate element model specific to the patient. A process performed by design generation system 240 for generating the baseplate element model (and models of other elements of an orthopedic prosthesis) is described elsewhere in this disclosure. In such examples, profile customization system 206 of planning system 126 may output a profile customization user interface for display. Profile customization system 206 may receive indications of user input via the profile customization user interface to customize the baseplate profile.

Figure 4:
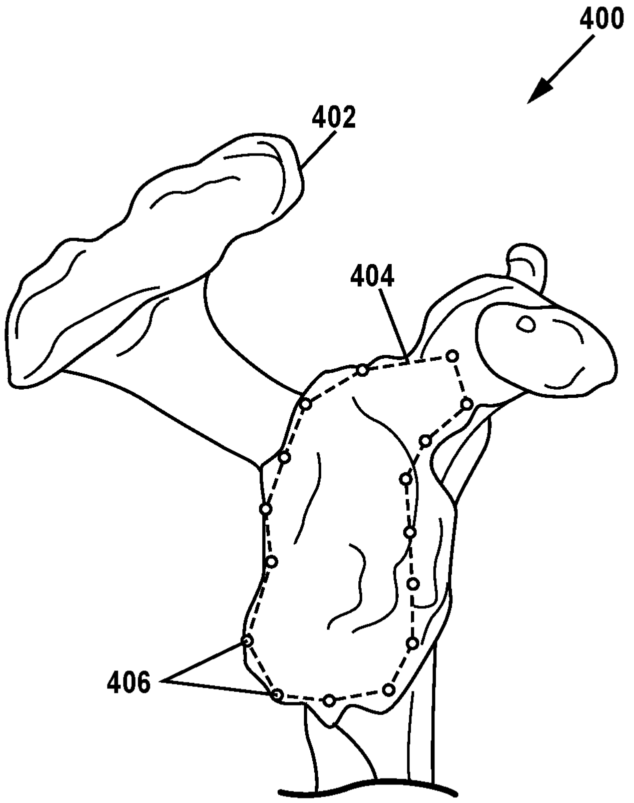
FIG. 4 is a conceptual diagram illustrating an example baseplate profile customization interface according to techniques of this disclosure.

FIG. 4 is a conceptual diagram illustrating an example baseplate profile customization interface 400 according to techniques of this disclosure. Baseplate profile customization interface 400 is a user interface that includes a 3D bone model 402 representing a bone of the patient. In the example of FIG. 4, the bone is a scapula. Additionally, baseplate profile customization interface 400 includes a baseplate profile 404 and a set of control points 406. In the example of FIG. 4, control points 406 are marked as circles. For simplicity, only some of control points 406 are marked with reference numerals. In some examples, baseplate profile 404 may initially be based on the baseplate size selected by the clinician and/or identified by prosthesis sizing system 204. Profile customization system 206 may update baseplate profile 404 in response to receiving indications of user input to manipulate control points 406. For example, profile customization system 206 may update baseplate profile 404 in response to receiving a drag-and-drop input to one of control points 406. In this way, the clinician can modify baseplate profile 404 in accordance with their preferences. For instance, the clinician can modify baseplate profile 404 to include additional areas for fixation of the baseplate element. Profile customization system 206 may fit a spline to control points 406 to obtain a smooth line connecting control points 406.

In response to receiving an indication of user input to manipulate control points 406 (or other input to modify baseplate profile 404), profile customization system 206 may apply one or more profile customization models 224 to adjust the baseplate profile. In some examples, profile customization models 224 include a generative model, such as a variational autoencoder (VAE) or generator of a generative adversarial network (GAN). Examples of such generative models are described in greater detail elsewhere in this disclosure. In the example of FIG. 2, profile customization system 206 includes a design generation system 240 that generates and selects one or more designs of the baseplate element that conform to the modified baseplate profile. An example of a design generation system is provided below with respect to FIG. 7.

An example process for customizing baseplate profile 404 uses an autoencoder network based on the techniques described in Umetani, "Exploring generative 3D shapes using autoencoder networks" (2017). In this example, profile customization system 206 may represent a baseplate element as a quad mesh parameterized as a vector of coordinates (e.g., cartesian coordinates, polar coordinates, etc.). In this example, profile customization models 224 may include an autoencoder trained to reconstruct vectors of coordinates provided as input. Profile customization system 206 may apply an encoder model of the autoencoder to the vector of coordinates representing the baseplate element. The encoder model of the autoencoder generates a latent space vector based on the vector of coordinates. The decoder model of the autoencoder may reconstruct the vector of coordinates based on the latent space vector.

When profile customization system 206 receives an indication of user input to adjust the position of one of control points 406 of baseplate profile 404, profile customization system 206 may modify one or more values in the latent space vector based on the adjusted position of the control element. Profile customization system 206 may optimize the latent space vector to minimize an error between the adjusted position of the control element and a position on the output baseplate profile generated when the decoder model is applied to the modified latent space vector. Profile customization system 206 may calculate the error as:

$$E(q) = \|x_i(q) - x_i'\|_2$$

where q is the latent space vector, $x_i(q)$ is a vertex of the output baseplate profile, and $x'_i$ is the adjusted position of the control element. Profile customization system 206 may compute a gradient of E relative to the modified latent space vector. Profile customization system 206 may then update a parameter in the modified latent space vector using Newton-Raphson iterations as:

$$q := E(q)\left(\frac{\partial E}{\partial q}\right) \Big/ \|\partial E / \partial q\|^2$$

For each update of the modified latent space vector, profile customization system 206 may project each element of q between 0 and 1 if the element exceeds the range of 0 to 1. Profile customization system 206 may apply the decoder model to the modified latent space vector and evaluates the output of the decoder model using the error function indicated above. Profile customization system 206 may continue iterating this manner until the error is minimized or otherwise reaches convergence.

Furthermore, in the example of FIG. 2, anchorage planning system 208 of planning system 126 may predict an arrangement of fixation holes defined in the baseplate element. The fixation holes are holes in the baseplate element through which fixation elements (e.g., screws, pegs, etc.) are passed to secure the baseplate element to the patient's scapula. In some examples, ML models 130 include one or more anchorage design models 226. Anchorage planning system 208 may apply anchorage design models 226 to predict the arrangement of fixation holes defined in the baseplate element. In some examples, anchorage planning system 208 may use a mathematical optimization process that evaluates various arrangements of fixation holes in the baseplate element to minimize or maximize a cost function. In such examples, the cost function may be a distance of functional components (e.g., fixation elements) to cortical bone. The cost function may penalize arrangements in which fixation elements penetrate through both sides of a bone.

Figure 5A:
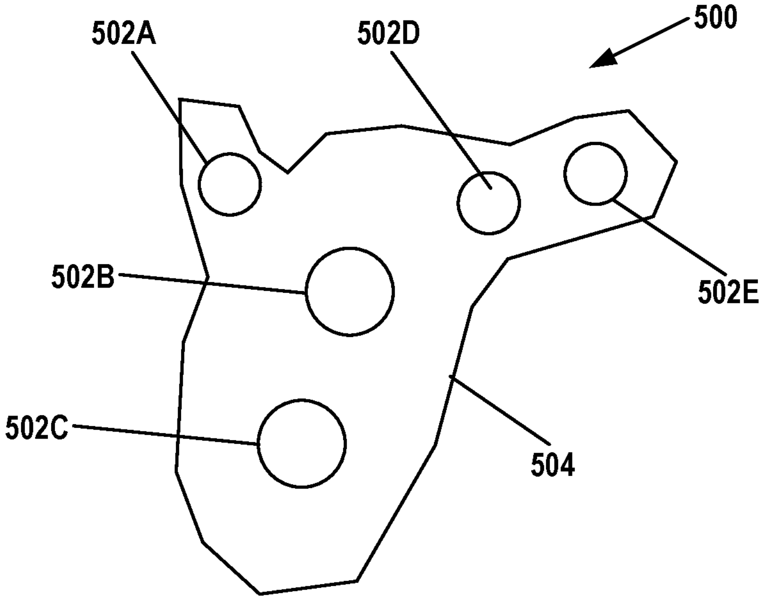
FIG. 5A and FIG. 5B are conceptual diagrams illustrating an example user interface that enables a clinician to select positions of fixation holes defined in a baseplate element according to techniques of this disclosure.
Figure 5B:
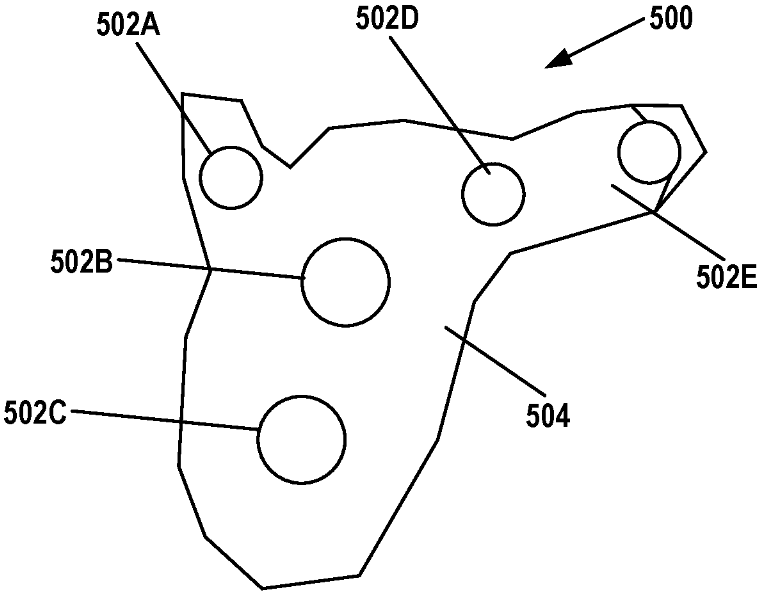

In some examples, anchorage planning system 208 outputs a user interface that enables a clinician to select positions of the fixation holes defined in the baseplate element. For instance, FIG. 5A and FIG. 5B are conceptual diagrams illustrating an example user interface 500 that enables a clinician to select positions of fixation holes 502A-502E (collectively, "fixation holes 502") defined in a baseplate element 504 according to techniques of this disclosure. Anchorage planning system 208 may receive indications of user input to adjust the positions of fixation holes 502. For instance, anchorage planning system 208 may receive indications of drag-and-drop input to move one of fixation holes 502. The clinician may want to change the positions of fixation holes 502 in order to ensure that the fixation elements enter higher quality bone.

In some examples, anchorage planning system 208 may receive an indication of user input to move a fixation hole beyond the outline of baseplate element 504. In some such examples, anchorage planning system 208 may automatically update the outline of baseplate element 504 to encompass the fixation hole. For instance, in the example of FIG. 5A and FIG. 5B, anchorage planning system 208 has moved fixation hole 502E outside the outline of baseplate element 504. Accordingly, anchorage planning system 208 has updated the outline of baseplate element 504 to encompass the updated position of fixation hole 502E.

In some examples, anchorage planning system 208 may automatically determine angles and/or depths of fixation elements. Selecting an appropriate angle and depth of a fixation element may be important so that the fixation element engages with high quality bone capable of serving as a secure attachment point for the glenoid prosthesis. In some examples, to determine the angles and/or depths of the fixation elements, anchorage planning system 208 may analyze a bone density map of the patient's bone (e.g., scapula) to identify areas of bone dense enough to support the fixation elements. Anchorage planning system 208 may draw lines connecting the identified areas of the planned fixation holes. In some examples, anchorage planning system 208 provides a user interface that receives indications of user input to modify the angles and/or depths of the fixation elements determined by anchorage planning system 208. In some examples, anchorage planning system 208 receives indications of user input to select angles and/or depths of the fixation elements without anchorage planning system 208 automatically determining the angles and/or depths of the fixation elements.

Figure 7:
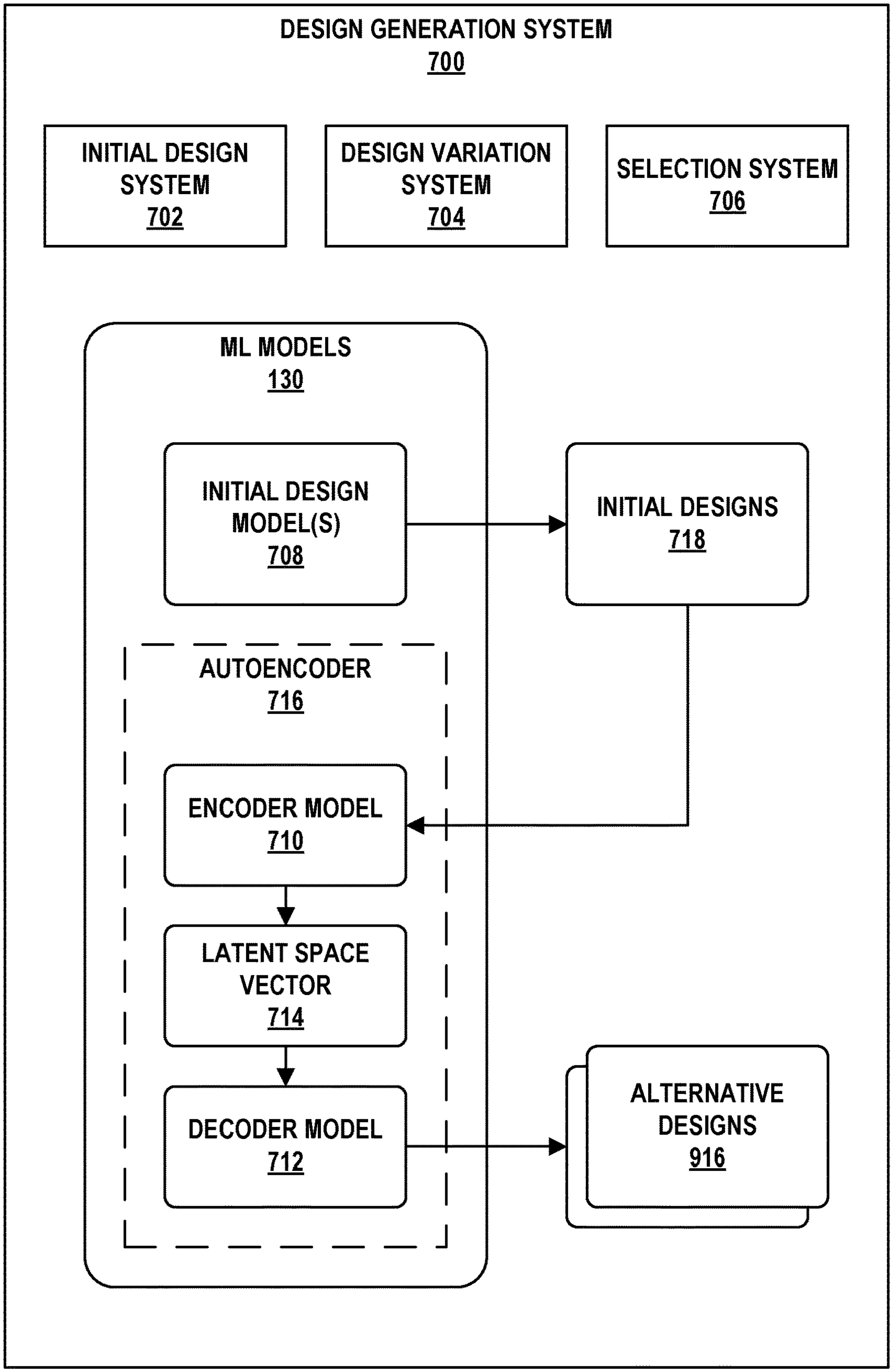
FIG. 7 is a block diagram illustrating an example of design generation system according to techniques of this disclosure.

Anchorage planning system 208 may use a design generation system 242 to generate a design of a baseplate element and/or augmentation element having the baseplate outline, selected fixation holes, and/or selected fixation angles. FIG. 7, which is described in detail below, describes an example design generation system suitable for generating the design. Anchorage planning system 208 may output the generated design for review and further adjustment by the clinician.

In some examples, anchorage planning system 208 may use an autoencoder to determine the updated outline of a baseplate element. For instance, in such examples, an autoencoder may be trained to recreate outlines of baseplate elements. Anchorage planning system 208 may receive an indication of user input to reposition a fixation hole at a particular location outside a current outline of the baseplate element. In response, anchorage planning system 208 may calculate new minimum boundary points. The new minimum boundary points are positions of one or more points having at least a minimum distance from an outer boundary of the repositioned fixation hole. Anchorage planning system 208 may provide the current outline of the baseplate element as input to an encoder model of an autoencoder. Anchorage planning system 208 may perform an optimization process on the values of features in a feature vector generated by the encoder model. When performing the optimization process, anchorage planning system 208 generates a plurality of trial feature vectors. Each of the trial feature vectors is a variation on the feature vector generated by the encoder model. Anchorage planning system 208 may apply the decoder model of the autoencoder to the trial feature vectors to generate a plurality of alternative outlines of the baseplate element. Anchorage planning system 208 may evaluate the alternative outlines to select one of the alternative outlines. In some examples, anchorage planning system 208 evaluates the alternative outlines by calculating a sum of distances between the new minimum boundary points and closest points in the alternative outlines. Anchorage planning system 208 may then select the alternative outline having the smallest calculated sum of distances.

Augmentation planning system 210 of planning system 126 may identify a 3D shape that occupies a space between the outline of the baseplate in the reference plane and the patient's (morbid) scapula. In other words, augmentation planning system 210 may define a 3D volume to fill the space between the reference plane and the glenoid surface. The identified 3D shape corresponds to an augmentation element of a glenoid prosthesis. The augmentation element of the glenoid prosthesis fills the space between the patient's scapula and the baseplate of the glenoid prosthesis. The augmentation element may include porous material, solid material, or a combination of porous and solid materials. In some examples, augmentation planning system 210 receives indications of user input to control thicknesses of porous and solid materials in the augmentation element.

In some examples, the augmentation element (e.g., a measured from the bone to the baseplate) does not occupy the entire area between the baseplate and the scapula. For instance, the augmentation element may occupy the entire area between the baseplate and the remaining bone of the glenoid fossa, but in examples where the baseplate is also anchored to the acromion process or coracoid process, the augmentation element does not need to occupy the entire area from the baseplate back to the base of the acromion process or base of the coracoid process. Rather, the augmentation element may be thinner in such areas. Thus, for regions outside glenoid fossa (e.g., outside the taper), augmentation planning system 210 may use a thickness rule related to a minimum thickness needed to accommodate anchorage fixation.

Figure 9:
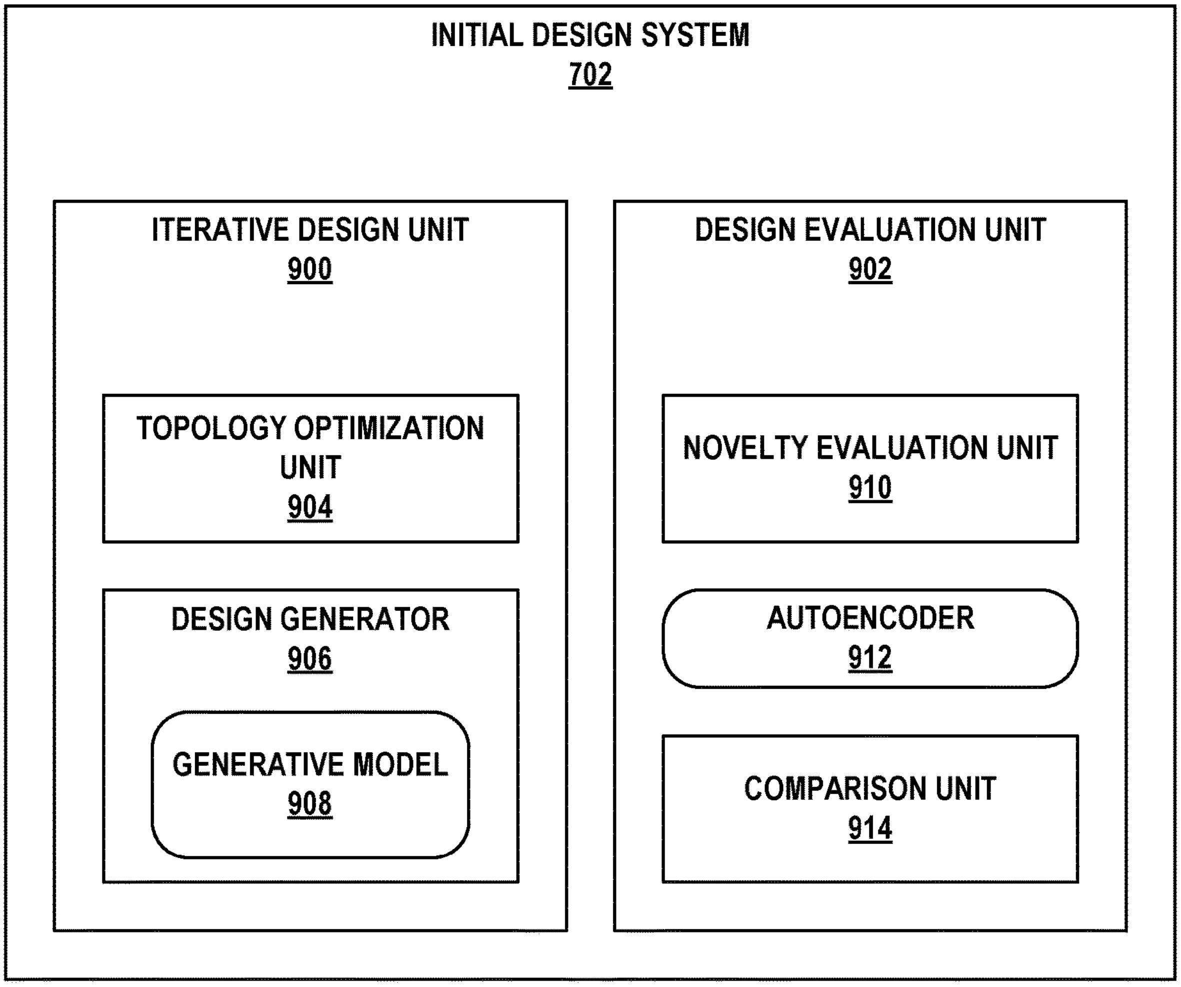
FIG. 9 is a block diagram illustrating an example initial design system according to techniques of this disclosure.

In some examples, such as the example of FIG. 2, augmentation planning system 210 includes a design generation system 244 that generates designs for augmentation elements. FIG. 9, which is described in detail below, describes an example design generation system suitable for generating designs for augmentation elements.

In some examples, planning system 126 operates in a fully automatic mode. When operating in the fully automatic mode, planning system 126 may use one or more of case classification system 200, premorbid modeling system 202, prosthesis sizing system 204, profile customization system 206, anchorage planning system 208, augmentation planning system 210 to generate a prosthesis model or components thereof. In other examples, planning system 126 may receive input from a clinician at various points in the process. For instance, in some examples, planning system 126 may receive an indication of user input that identifies a classification of the orthopedic prosthesis of the patient. In such examples, planning system 126 does not use case classification system 200. In some examples, premorbid modeling system 202 determines a joint line without input from the clinician. In other examples, premorbid modeling system 202 determines the joint line based at least in part on input from the clinician. In some examples, prosthesis sizing system 204 determines a size of the prosthesis without input from the clinician.

Figure 6:
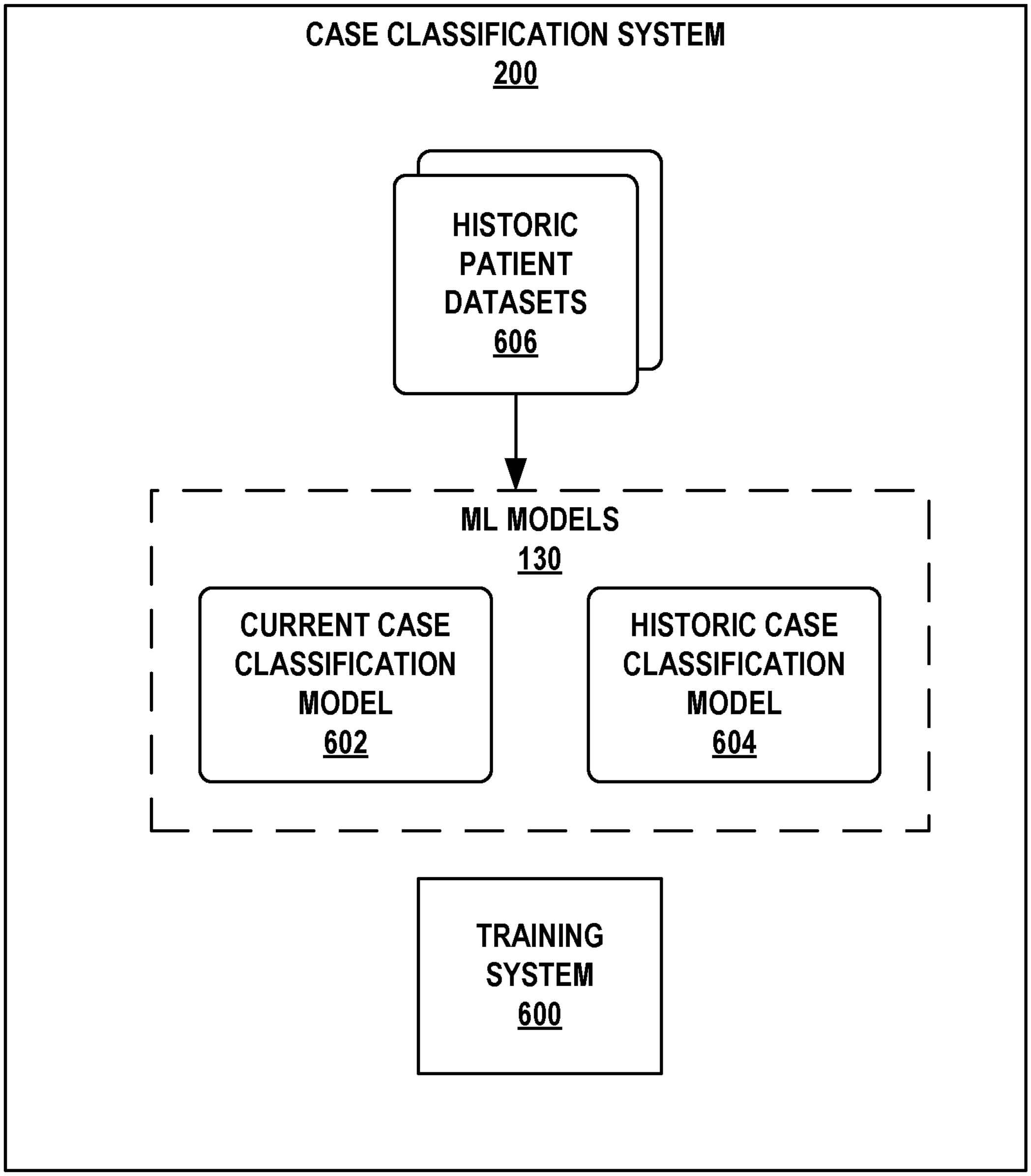
FIG. 6 is a block diagram illustrating an example case classification system according to techniques of this disclosure.

FIG. 6 is a block diagram illustrating an example case classification system 200 according to techniques of this disclosure. In the example of FIG. 6, ML models 130 include a current case classification model 602 and a historic case classification model 604. Case classification system 200 applies current case classification model 602 to data for a specific patient to generate a classification of an orthopedic prosthesis to implant in the specific patient. Example classifications may include patient-matched implants, patient-specific implants, complex patient-matched implants, and custom implants. In some examples, current case classification model 602 generates a classification of the specific patient according to anatomical deformity level and/or level of bone loss. In some examples, current case classification model 602 classifies a location and amount of bone loss on an articular surface, e.g., for primary or revision cases. In some examples, planning system 126 may present the classification for review by a clinician. The clinician may consider the classification when planning an orthopedic surgery for the specific patient. For example, if the classification of the orthopedic prosthesis to implant in the specific patient is a complex patient-matched implant, the surgeon may begin a workflow to design a complex patient-matched implant for the specific patient. In some examples, planning system 126 may automatically begin a workflow to design an orthopedic prosthesis of the classification generated by current case classification model 602 without further input from the clinician.

Input to current case classification model 602 may include a bone model of a patient. The bone model of the patient may represent one or more bones of the patient. In some examples, inputs to current case classification model 602 may include additional data regarding the patient. The additional data regarding the patient may include data indicating one or more of activities of the patient, age of the patient, sex of the patient, occupation of the patient, soft tissues of the patient, outcome expectations of the patient, and so on.

Current case classification model 602 may be implemented in one of a variety of ways. For example, current case classification model 602 may be a deep learning model, such as a deep neural network. The bone models used as inputs to current case classification model 602 may be differently formatted for different types of deep learning models. For example, current case classification model 602 may be a voxel-based deep learning model that takes a voxel-based representation of the bone model as input. In another example, current case classification model 602 may be a point cloud-based deep learning model that takes a point cloud-based representation of the bone model as input. In another example, current case classification model 602 may be a multiview-based deep learning model that takes as input a bone model that includes multiple 2-dimensional views of the one or more bones. In another example, current case classification model 602 may be a deep learning model that takes as input a bone model that represents the one or more bones as mesh data. In some examples where current case classification model 602 is a voxel-based deep learning model, current case classification model 602 may be based on a VoxNet model, PointNet model, MeshNet model, or a multi-view-based model.

In some examples, current case classification model 602 may include a perceptron layer that follows layers of current case classification model 602 that classify the bone model. Inputs to the perceptron layer may include a classification based on the bone model and may also include other patient data. The other patient data may include information related to the age of the patient, sex of the patient, expected activities of the patient, and so on. A max pooling layer may follow the perceptron layer. The output of the max pooling layer may therefore indicate a predicted classification of the orthopedic prosthesis for the patient.

A training system 600 of case classification system 200 may use training data to train current case classification model 602. In some examples, training system 600 is omitted from production versions of case classification system 200. The training data may include training data pairs. Each training data pair may include training input data and expected output data. The training input data may include the same types of input as provided to current case classification model 602. For instance, the training input data may include a bone model of a patient (and, in some examples, additional data regarding a patient). The expected output data of a training data pair may specify a classification of an orthopedic prosthesis to be implanted in the patient. Training system 1200 may apply current case classification model 602 to the training input data of a training data pair to obtain a predicted classification. Training system 1200 may generate a loss value by applying a loss function to the predicted classification and the classification specified by the expected output data of the training data pair. Training system 1200 may use a backpropagation process to modify weights in current case classification model 602 based on the loss value.

The accuracy of current case classification model 602 may improve by training current case classification model 602 using larger numbers of training data pairs. However, it may be difficult or expensive to obtain large numbers of training data pairs. In accordance with techniques of this disclosure, training system 600 may use historical patient datasets 606 to generate training data pairs. Patient datasets 118 (FIG. 1) may include historical patient datasets 606. Each of historical patient datasets 606 includes data regarding a particular patient who has undergone an orthopedic surgery that involved implantation of an orthopedic prosthesis. There may be many such historical patient datasets 606. However, historical patient datasets 606 might not include data specifying classifications of the orthopedic prostheses implanted in the patients. Example classifications may include patient-matched implants, patient-specific implants, complex patient-matched implants, and custom implants. Nevertheless, historical patient datasets 606 may be valuable as a source of training data for training a current case classification model 602 to recommend a classification of an orthopedic prostheses to implant in a current patient.

Accordingly, training system 600 may apply historic case classification model 604 to historic patient datasets 606 to determine classifications of the orthopedic prostheses implanted in the patients. For example, training system 1200 may apply historic case classification model 604 to a historic patient dataset for a specific patient to determine that the classification of orthopedic prosthesis implanted in the specific patient was a complex patient matched implant.

In some examples, historic patient datasets 606 include bone models, prosthesis models, and other data. Input to historic patient classification model 604 includes a bone model and a prosthesis model. The bone model may represent one or more bones of a patient. The prosthesis model may represent a prosthesis implanted in the patient. In some examples, inputs to historic case classification model 604 may include additional data regarding the patient. The additional data regarding the patient may include data indicating one or more of activities of the patient, age of the patient, sex of the patient, occupation of the patient, soft tissues of the patient, outcome expectations of the patient, and so on. In some examples, the additional data regarding the patient may include prosthesis performance data. The prosthesis performance data may include data indicating one or more of a preoperative patient range of motion simulation, post-operative patient range of motion measurements, and patient-reported outcome measurements. In some examples, the inputs to historic case classification model 604 include data indicating anatomy and deformity correction, such as a final joint line, bone removal, seating ratios, and so on.

Historic case classification model 604 may be implemented in one of a variety of ways. For example, historic case classification model 604 may be a deep learning model, such as a deep neural network. The bone models used as inputs to historic case classification model 604 may be differently formatted for different types of deep learning models. For example, historic case classification model 604 may be a voxel-based deep learning model that takes a voxel-based representation of the bone model and prosthesis model as input. In another example, current case classification model 602 may be a point cloud-based deep learning model that takes a point cloud-based representation of the bone model and prosthesis model as input. In another example, current case classification model 602 may be a multiview-based deep learning model that takes as input a bone model that includes multiple 2-dimensional views of the one or more bones and prosthesis. In another example, current case classification model 602 may be a deep learning model that takes as input a bone model that represents the one or more bones and/or prosthesis as mesh data.

In an example where historic case classification model 604 is a voxel-based deep learning model, inputs to historic case classification model 604 may include a 3-dimensional grid of voxels. Individual voxels within the 3-dimensional grid may be different values to indicate whether the voxel corresponds to bone, prosthesis, or space unoccupied by bone or the prosthesis. For instance, in one example, a voxel having a value of 1 corresponds to a location within the prosthesis, a voxel having a value of 2 corresponds to a location within a bone, a voxel having a value of 3 indicates regions of interest of the anatomy of the patient, and a voxel having a value of 0 indicates other (or unoccupied) areas. In another example, a voxel having a value of 1 corresponds to a first bone (e.g., a scapula), a voxel having a value of 2 corresponds to a second bone (e.g., a humerus), and a voxel having a value of 0 corresponds to background.

Training system 600 may use training data to train historic case classification model 604. The training data used to train historic case classification model 604 may include training data pairs. Each training data pair may include training input data and expected output data. The training input data may include the same types of input as provided to historic case classification model 604. For instance, the training input data may include a bone model of a patient, a prosthesis model of the patient, and, in some examples, additional data regarding the patient. The expected output data of a training data pair may specify a classification of an orthopedic prosthesis that was implanted in the patient or should have been implanted in the patient instead of the orthopedic prosthesis that was implanted in the patient. Trained humans may identify the classification of the orthopedic prosthesis that was implanted in the patient or should have been implanted in the patient. A human may determine that a different type of orthopedic prosthesis should have been implanted in the patient by evaluating the prosthesis performance data for the patient. Training system 600 may apply historic case classification model 604 to the training input data of a training data pair to obtain a predicted classification. Training system 600 may generate a loss value by applying a loss function to the predicted classification and the classification specified by the expected output data of the training data pair. Training system 600 may use a back-propagation process to modify weights in historic case classification model 604 based on the loss value.

FIG. 7 is a block diagram illustrating an example of design generation system 700 according to techniques of this disclosure. In the example of FIG. 7, design generation system 700 includes an initial design system 702, a design variation system 704, and a selection system 706. In the example of FIG. 7, ML models 130 of planning system 126 (FIG. 1) include one or more initial design models 708, an encoder model 710, and a decoder model 712. As described in detail below, encoder model 710, decoder model 712, and a latent space vector 714 may form part of an autoencoder 716.

Different instances of design generation system 700 may be configured for different purposes. For example, design generation system 700 may be included in profile customization system 206 (FIG. 2) and configured to generate customized baseplate element designs. In another example, design generation system 700 may be included in anchorage planning system 208 (FIG. 2) and configured to generate baseplate element designs and/or augment element designs having specified fixation holes and/or fixation angles. In another example, design generation system 700 may be an instance of prosthesis design generation system configured to a design for a complete orthopedic prosthesis.

In the example of FIG. 7, initial design system 702 of design generation system 700 generates one or more initial designs 718. Each of initial designs 718 may represent a design of an orthopedic prosthesis or component thereof. For instance, initial designs 718 may represent an augmentation element of a glenoid prosthesis, a baseplate element of the glenoid prosthesis, and/or other elements of a glenoid prosthesis. In some examples, an initial prosthesis design includes a 3-dimensional model of an orthopedic prosthesis. In some examples, an initial prosthesis design may include a plurality of 2-dimensional images of an orthopedic prosthesis. Initial design system 702 may apply one or more initial design models 708 to generate initial designs 718. An example of initial design system 702 is provided below with respect to FIG. 9. Design variation system 704 may apply encoder model 710 to initial designs 718 to generate latent space vector 714. Additionally, design variation system 704 may modify latent space vector 714. Design variation system 704 may apply decoder model 712 to the modified latent space vectors to generate alternative designs 720. Selection system 706 may evaluate alternative designs 720 to select a prosthesis (or prosthesis components) for the patient.

Figure 8:
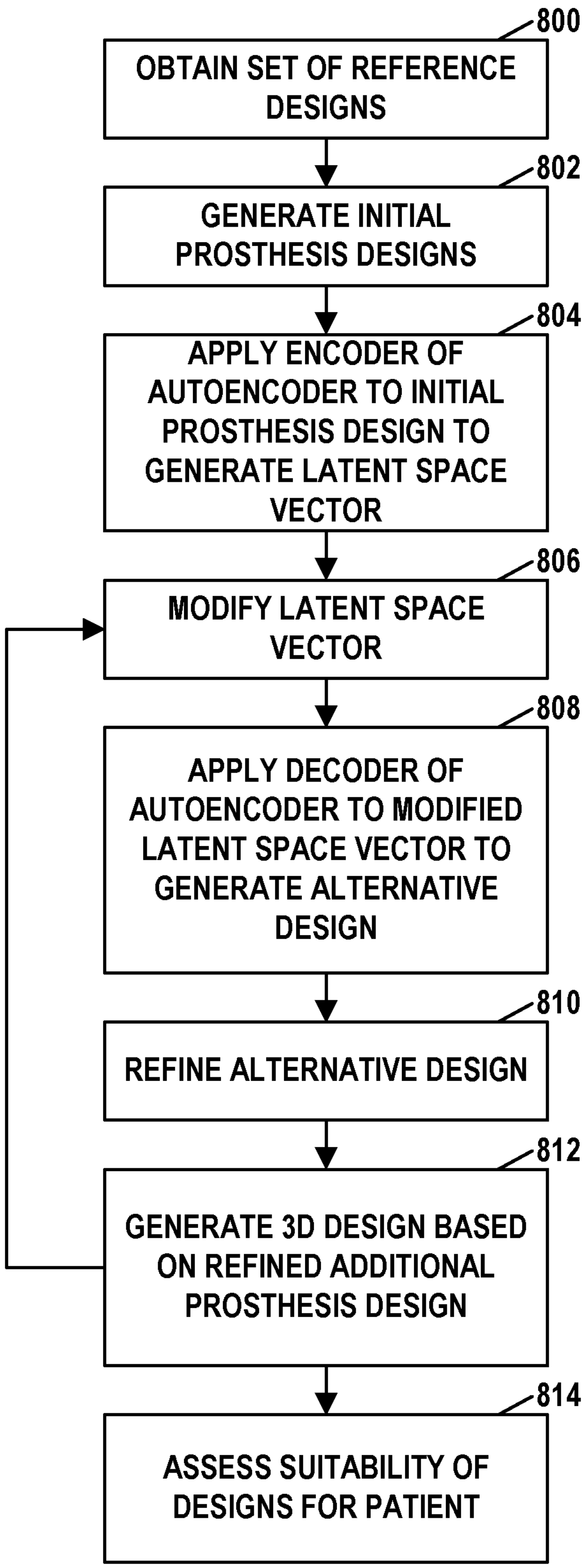
FIG. 8 is a flowchart illustrating an example operation of design generation system according to techniques of this disclosure.

FIG. 8 is a flowchart illustrating an example operation of design generation system 700 according to techniques of this disclosure. In the example of FIG. 8, planning system 112 obtains a set of reference designs (800). In some examples, the set of reference designs may include designs of orthopedic prostheses previously implanted in patients. In some examples where design generation system 700 is generating a design of a baseplate element, the set of reference designs include a set of baseplate element designs. In some examples where design generation system 700 is generating a design of an augmentation element, the set of reference designs include a set of augmentation element designs.

Furthermore, initial design system 702 of planning system 126 may generate one or more initial designs 718 (802). ML models 130 may include one or more initial design models 708 that initial design system 702 may apply to generate the initial designs 718. An example implementation of initial design system 702 and an example process for generating the initial prosthesis designs are described with respect to FIG. 9 and FIG. 10, respectively.

Furthermore, in the example of FIG. 8, after initial design system 702 generates a preliminary prosthesis model, design variation system 704 may apply encoder model 710 of autoencoder 716 to one or more of initial designs 718 to generate latent space vector 714 (804). Encoder model 710 is an ML model that generates latent space vector 714 based on the preliminary prosthesis model. Latent space vector 714 has reduced dimensionality relative to the initial design provided as input to encoder model 710. For example, the initial design may be a 128×128×128 3D image. Hence, the dimensionality of the initial design may be 2,097,152. In this example, latent space vector 714 may have a dimensionality of 128. In other words, latent space vector 714 may be a vector that comprises 128 elements. Thus, in this example, encoder model 710 maps a 128×128×128 3D image into a 128-dimensional latent space.

After design variation system 704 has generated latent space vector 714, design variation system 704 may generate a modified latent space vector based on latent space vector 714 (806). For example, design variation system 704 may increase or decrease one or more elements in latent space vector 714 to generate a modified latent space vector. Design variation system 704 may apply decoder model 712 of autoencoder 716 to the modified latent space vector to generate an alternative design (808). In other words, design variation system 704 may provide the modified latent space vector as input to decoder model 712.

Furthermore, design variation system 704 may refine the alternative design (810). For example, design variation system 704 may smooth and sharpen edges of the alternative design, extract edges of the alternative design, convert the edges of the alternative design into coordinate data, and group the coordinates of the edges. Design variation system 704 may group the edge coordinates based on their continuity (e.g., using a Freeman Chain) or any other order. Design variation system 704 may generate a 3D design based on the refined alternative design (812). For instance, the refined alternative design may include a set of 2-dimensional images and a cross-section image. Design variation system 704 may use the 2-dimensional images and the cross-section image to generate a 3-dimensional design.

Design variation system 704 may repeat actions 806 through 812 multiple times. Thus, by applying decoder model 712 to a plurality of modified feature vectors, design variation system 704 may generate a plurality of alternative designs 916. An example implementation of encoder model 710 and decoder model 712 is described below with respect to FIG. 11. In some examples, initial designs 718 and alternative designs 916 comprise computer assisted design (CAD) data.

Selection system 706 may assess the suitability of designs (e.g., initial designs 718 and/or alternative designs 916) for the patient (814). For example, selection system 706 may apply a cost function to the designs to determine cost values for the designs. Selection system 706 may select a design based on the cost values for the designs. For example, selection system 706 may select the design having the lowest cost value.

The cost function may be based on various types of data. For example, for each of the designs, selection system 706 may determine a set of factor values. In this example, the factor values are parameters of the cost function. In other words, selection system 706 may determine the cost value for a design based on the factor values. In some examples, the factor values include one or more values characterizing a range of motion associated with the design. In some examples, the factor values include a value characterizing an amount of bone that must be removed in order to implant a prosthesis based on the design. In some examples, the factor values may include one or more values characterizing a seating, lateralization, version angle, or inclination angle of a glenoid prosthesis based on the design. Penalizing designs based on these factor values may result in selection system 706 selecting a design associated with the greatest range of motion, best seating, and least lateralization, version angle, and inclination angle, least bone loss, and so on.

FIG. 9 is a block diagram illustrating an example initial design system 702 according to techniques of this disclosure. In the example of FIG. 9, initial design system 702 is an adaptation of the deep generative design framework described in Oh et al., "Deep Generative Design: Integration of Topology Optimization and Generative Models," arXiv: 1903.01548. However, in other examples, other generative design frameworks may be used. In the example of FIG. 9, initial design system 702 includes an iterative design unit 900 and a design evaluation unit 902. Iterative design unit 900 performs an iterative design exploration process that generates new designs based on reference designs. The designs may be designs of baseplate elements, designs of augmentation elements, designs for arrangements of fixation holes, designs for complete prostheses, and so on. Design evaluation unit 902 evaluates the new designs generated by iterative design unit 900. In the example of FIG. 9, iterative design unit 900 includes a topology optimization unit 904 and a design generator 906. As described in greater detail below with respect to FIG. 10, topology optimization unit 904 performs a topology optimization process that generates new designs. Design generator 906 may use the new designs to train a generative model 908. After design generator 906 has trained generative model 908, design generator 906 may apply generative model 908 to generate additional new designs.

Furthermore, in the example of FIG. 9, design evaluation unit 902 includes a novelty evaluation unit 910, an autoencoder 912, and a comparison unit 914. Novelty evaluation unit 910 analyzes new designs to determine novelty scores for the new designs. The novelty score for a new prosthesis design indicates a degree of difference from any of the reference designs. Autoencoder 912 has been trained to reconstruct the reference designs. Novelty evaluation unit 910 may use autoencoder 912 to determine the degrees of difference of the new reference designs. In general, autoencoder 912 is able to better reconstruct a new design if the new reference design is less novel as compared to the reference designs. Conversely, autoencoder 912 is less able to accurately reconstruct a new design if the new reference design is more novel as compared to the reference designs. Comparison unit 914 may evaluate the reference designs and new designs to select initial designs 718.

Figure 10:
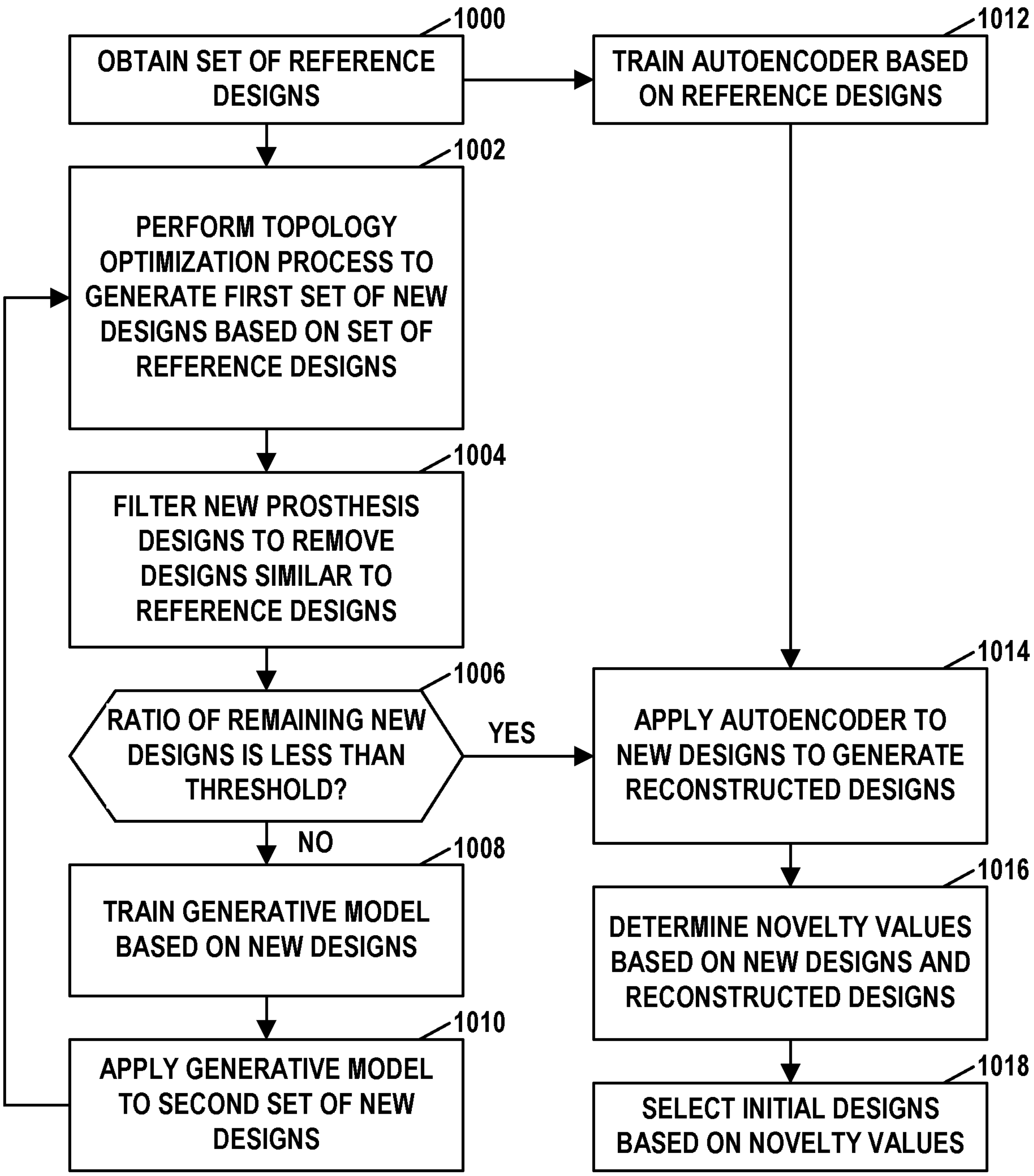
FIG. 10 is a flowchart illustrating an example operation of initial design system according to techniques of this disclosure.

FIG. 10 is a flowchart illustrating an example operation of initial design system 702 according to techniques of this disclosure. As mentioned above, initial design system 702 may perform an iterative design exploration process and a design evaluation process. In the example of FIG. 10, the iterative design exploration process is shown in the left column and the design evaluation process is shown in the right column. During the iterative design exploration process, initial design system 702 may use topology optimization and generator ML models to generate new designs. During the design evaluation process, initial design system 702 evaluates designs generated during the iterative design exploration process.

In the example of FIG. 10, initial design system 702 may obtain a set of reference designs (1000). The set of reference designs may include designs of orthopedic prostheses (or components, such as baseplate elements, augmentation elements, etc.) previously implanted in patients. The iterative design exploration process includes generating new designs based on a set of reference designs. In some examples, the reference designs may be models of orthopedic prostheses previously implanted into patients. For instance, in some examples where design generation system 700 generates designs of baseplate elements, the reference designs are designs of baseplate elements of orthopedic implants previously implanted into patients. In some examples, initial design system 702 obtains the reference designs from historic patient datasets (e.g., historic patient datasets 606 (FIG. 6)).

Topology optimization unit 904 may perform a topology optimization process to generate new prosthesis designs based on the reference prosthesis designs (1002). For instance, as part of generating a new prosthesis design, topology optimization unit 904 may apply a solid isotropic material with penalization (SIMP) procedure. Conceptually, in the SIMP procedure, a domain is discretized into a grid of finite elements. Each element of the grid can have values ranging from 0 to 1, with 0 representing an area unoccupied by material and 1 representing occupied by material. Intermediate values between 0 and 1 may correspond to material with lesser density. Boundaries of the grid correspond to edges of the space that can be occupied by the orthopedic prosthesis. For instance, in an example where design generation system 700 is generating a baseplate element profile, the boundaries of the grid bay correspond to an outline of specified by a predetermined baseplate element size (e.g., as shown in FIG. 3) or selected by a clinician (e.g., as shown in FIG. 4). In an example where design generation system 700 is generating an augmentation element of a glenoid prosthesis, the boundaries of the grid may correspond to a space between a joint line and a bone of a patient and a profile of a baseplate element of the glenoid prosthesis. The SIMP procedure penalizes intermediate density values, resulting in a distribution of values equal to 0 and 1.

Furthermore, as part of performing the SIMP procedure, topology optimization unit 904 may optimize the prosthesis model for stiffness. To do so, topology optimization unit 904 may start with a random distribution of values in the grid that satisfies a target mass constraint, a global force-stiffness equilibrium, and required functional constraints. Topology optimization unit 904 may then perform a series of iterations. During each iteration, topology optimization unit 904 may calculate a similarity metric (e.g., a stiffness value) based on a comparison of the current topology to a topology of an existing orthopedic prosthesis, such as orthopedic prostheses from multiple manufacturers. Topology optimization unit 904 may then modify one or more values in the grid, subject to the constraints, and perform another iteration. The iterations may continue until one or more stopping criterion are reached, at which time, topology optimization unit 904 may select a topology with a highest similarity metric. Such comparisons may reduce deviation in the current topology from standard validated designs for orthopedic prostheses.

Iterative design unit 900 may filter the set of new designs to remove designs that are too similar to the reference designs (1004). After topology optimization unit 904 generates a set of new designs, iterative design unit 900 may determine whether a ratio of remaining new designs to reference designs to less than a threshold (1006). In general, the ratio of remaining new designs to reference designs drops below the threshold when a design space for designs has been sufficiently explored.

If the ratio of remaining new designs is not less than the threshold ("NO" branch of 1006), design generator 906 may train generative model 908 based on the remaining new designs (1008). As previously mentioned, generative model 908 may be a VAE, GAN, or other type of ML model configured to generate new prosthesis designs. In an example where generative model 908 is a GAN, design generator 906 may train generative model 908 to produce prosthesis models that a discriminator of the GAN would not be able distinguish from the new prosthesis designs generated using the SIMP procedure.

In some examples, the GAN is a Boundary Equilibrium GAN (BEGAN). In such examples, design generator 906 provides a random vector of latent variables as input to a design generator. A discriminator of the BEGAN may receive either prosthesis designs generated using the SIMP procedure or the output of the design generator. The discriminator may comprise an autoencoder that includes a discriminator encoder and a discriminator decoder. The discriminator encoder includes a convolutional neural network. The discriminator decoder and the design generator may be implemented as deconvolutional neural networks. In some examples, the discriminator decoder and the design generator have the same architecture. The discriminator processes an input (e.g., a design generated using the SIMP procedure or the output of the design generator) to reconstruct the input. Design generator 906 may apply a loss function to generate a loss value that quantifies differences between the reconstructed input and the input. Design generator 906 may use the loss value to retrain the design generator and the discriminator, e.g., using an Adam optimizer.

After training the generative model, design generator 906 may apply generative model 908 to generate a second set of new designs (1010). To apply generative model 908, design generator 906 may provide a random input to generative model 908 and perform a feedforward operation through generative model 908. Topology optimization unit 904 may use the second set of new designs as reference designs in another iteration of the iterative design exploration process. In this way, iterative design unit 900 may be able to generate numerous designs.

Novelty evaluation unit 910 of design evaluation unit 902 may train autoencoder 912 based on reference designs (1012). In other words, novelty evaluation unit 910 may train autoencoder 912 to reconstruct the reference designs. The reference designs may be the same or different from the reference designs initially used by iterative design unit 900. In examples where generative model 908 includes a BEGAN, autoencoder 912 may be implemented in the same way as the discriminator model of the BEGAN. If the ratio of new remaining prosthesis designs is less than the threshold ("YES" branch of 1006), novelty evaluation unit 910 may apply autoencoder 912 to the new prosthesis designs to generate reconstructed designs (1014). Novelty evaluation unit 910 may then determine novelty values for the new designs and the reconstructed designs (1016). For example, novelty evaluation unit 910 may determine the novelty values using a same loss function used to train autoencoder 912.

Comparison unit 914 of design evaluation unit 902 may select one or more initial designs 718 based on the novelty values and/or other data regarding the patient and/or the new designs (1018). At this stage of the design generation process, it is desirable to generate a diversity of designs. At the same time, compliance with constraints (e.g., to minimize bone removal, to align fixation holes with high quality bone, to align a lateral surface of the design with a joint line or reference plane) should also be maximized. Accordingly, comparison unit 914 may apply a function to generate a compliance score for the new designs. Comparison unit 914 may select initial design 718 having novelty values that exceed a first threshold and also have compliance scores that exceed a second threshold. In some examples, the first and second thresholds are configurable by a user.

Figure 11:
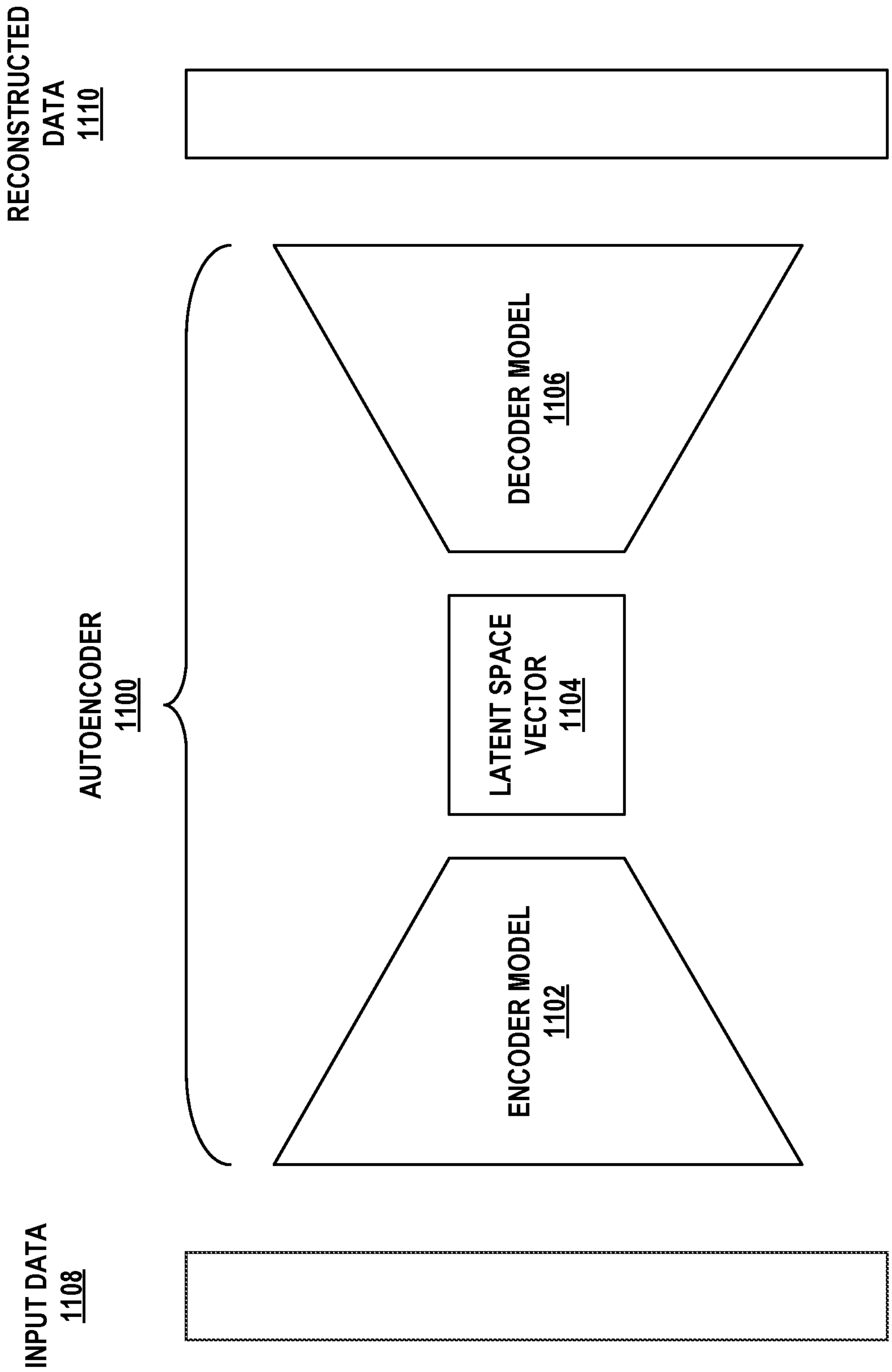
FIG. 11 is a conceptual diagram illustrating an example autoencoder according to techniques of this disclosure.

FIG. 11 is a conceptual diagram illustrating an example autoencoder 1100 according to techniques of this disclosure. Autoencoder 1100 may represent any of the autoencoder described elsewhere in this disclosure, such as autoencoder 716 (FIG. 7), autoencoder 912, and so on. As shown in the example of FIG. 11, autoencoder 1100 may include an encoder model 1102, a latent space vector 1104, and a decoder model 1106. Encoder model 1102 comprises a convolutional neural network (CNN). Decoder model 1106 comprises a deconvolutional neural network. Latent space vector 1104 stores the output of encoder model 1102. Input to decoder model 1106 includes data stored in latent space vector 1104. Latent space vector 1104 may include fewer features than either an input model 1108 or reconstructed data 1110. For instance, in some examples, latent space vector 1104 may be a buffer of 128 features. A feature may be a number.

Encoder model 1102 may include a series of layers. The layers of encoder model 1102 may include an input layer, one or more hidden layers, and an output layer. The hidden layers of encoder model 1102 may include one or more convolutional layers. Neurons in a convolutional layer are not connected to each value in an input matrix of the convolutional layer. Rather, neurons in a convolutional layer are connected to values in a receptive field with the input matrix of the convolutional layer. A neuron in a convolutional layer (i.e., a convolutional layer neuron) performs a convolution, such as a dot product, to generate an output value based on values generated by neurons in the receptive field of the convolutional layer neuron and weights of connections between the convolutional layer neuron and the neurons in the receptive field of the convolutional layer neuron. The hidden layers of encoder model 1102 may also include pooling layers, fully connected layers, or other types of layers. Each neuron in a pooling layer may have a receptive field and may output an aggregate value based on the values in the receptive field of the neuron. For instance, a neuron in a pooling layer may output a maximum value of the values in the receptive field of the neuron, an average of the values in the receptive field of the neuron, or another type of aggregate value.

Decoder model 1106 may include a series of layers. The layers of decoder model 1106 may include an input layer, one or more hidden layers, and an output layer. The hidden layers of decoder model 1106 may include one or more deconvolutional layers or transposed convolutional layers. A neuron in a deconvolutional layer, sometimes called "transposed convolution" layer, may generate an output value based on values in a padded receptive field and weights of connections between the neuron and locations in the receptive field of the neuron. The padded receptive field may include values generated by neurons in a previous layer of decoder model 1106 and padding values.

Input data 1108 may be provided as input to encoder model 1102. Input data 1108 may include various types of information and may have one of a variety of formats. In some examples, input data 1108 includes a 3D matrix in which each location within the 3D matrix indicates whether bone is present at the location. In some examples where input data 1108 is a 3D matrix, each location within the 3D matrix may include an intensity value or luma value, which may indicate a density of bone or absence of bone at the location. In some examples, input data 11108 represent a point cloud. For instance, input data 1108 may comprise an unstructured collection of point datasets. A point dataset may indicate coordinates of a point in the point cloud. The points in the point cloud may correspond to locations on a surface of a bone. In some examples, input data 1108 represents a design of a prosthesis or component of a prosthesis. Decoder model 1106 generates reconstructed data 1110 based on data in latent space vector 1104. Reconstructed data 1110 may be in the same or different format as input data 1108.

A training system may train autoencoder 1100 to minimize differences between input data 1108 and reconstructed data 1110. For example, the training system may use training data to train autoencoder 1100. The training data may include training datasets. Each of the training datasets of the training data may include a set of input data, such as a bone model, prosthesis design, prosthesis component design, data indicating a fixation hole arrangement, and so on. When training autoencoder 1100, the training system may apply autoencoder 1100 to input data in the training data to generate reconstructed input data. The training system may then apply an error function to determine a loss value. The loss value may correspond to an amount of difference between the input data and the reconstructed input data. For instance, the loss value may be a total of distances between each point of a design or model and the closest point of the reconstructed design or model. In some examples, the loss value may be a dice loss. The training system may perform a backpropagation process to update parameters (e.g., weights of connections between artificial neurons of autoencoder 1100) based on the loss value. In some examples, the loss value used for backpropagation is an average of loss values so calculated for multiple training datasets, ½ multiplied by a sum of squares of loss values so calculated for multiple training datasets, or a mean squared error of loss values so calculated for multiple training datasets. In this way, the training system trains both encoder model 1102 and decoder model 1106 of autoencoder 1100 so that autoencoder 1100 reconstructs the input data as close as possible to the input data of the training datasets.

Figure 12:
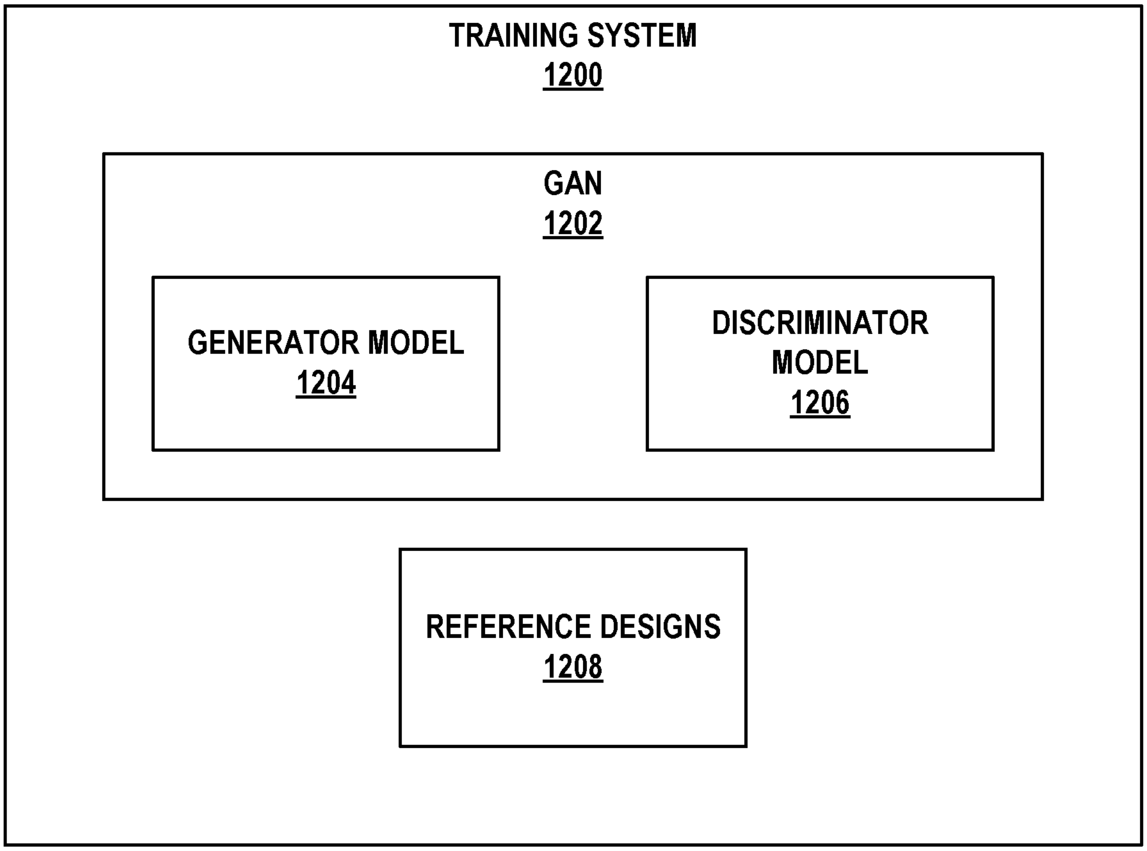
FIG. 12 is a block diagram illustrating example components of a training system for a generative adversarial network (GAN) accordance to techniques of this disclosure.

FIG. 12 is a block diagram illustrating example components of training system 1200 for a GAN 1202 accordance to techniques of this disclosure. As discussed above, generative model 908 and other ML models may be implemented using a GAN. In the example of FIG. 12, GAN 1202 includes a generator model 1204 and a discriminator model 1206.

Discriminator model 1206 may include a series of layers. The layers of discriminator model 1206 may include an input layer, one or more hidden layers, and an output layer. The hidden layers of discriminator model 1206 may include one or more convolutional layers or convolutional layers. A neuron in a convolutional layer may generate an output value based on values in a padded receptive field and weights of connections between the neuron and locations in the receptive field of the neuron. The padded receptive field may include values generated by neurons in a previous layer of discriminator model 1206 and padding values. In some examples, discriminator model 1206 may include five 5×5×5 convolutional layers plus an activation layer. Example activations functions may include a parametric rectified linear unit (PRELU) activation function, a rectified linear unit (ReLU) activation function, or other types of activation functions.

During training, generator model 1204 and discriminator model 1206 may form part of GAN 1202. Training system 1200 may be configured to perform a plurality of training iterations to train generator model 1204 and discriminator model 1206. For example, training system 1200 may alternate between performing one or more training epochs to train generator model 1204 and one or more training epochs to train discriminator model 1206. Training system 1200 may perform the plurality of training iterations during such a training epoch. During a training iteration, generator model 1204 may generate, based on input data for the training iteration, an output design for the training iteration. In some examples, generator model 1204 includes a deconvolutional model, similar to decoder model 1106 (FIG. 11). Generator model 1204 may generate designs. In some examples, generator model 1204 may be previously trained (e.g., as part of an autoencoder, such as autoencoder 1100 (FIG. 11) to generate designs based on reference designs 1208.

Discriminator model 1206 may generate, based on input provided to discriminator model 1206, a discriminator output for the training iteration. The discriminator output for the training iteration may comprise a level of confidence that generator model 1204 generated the discriminator input for the training iteration as opposed to the discriminator input being one of reference designs 1208. Training system 1200 may determine a loss value for the training iteration based on the discriminator output for the respective training iteration. Training system 1200 may update parameters of generator model 1204 or discriminator model 1206 based on the loss value for the respective training iteration.

In some examples, training system 1200 may alternate between performing one or more training epochs to train generator model 1204 and one or more training epochs to train discriminator model 1206. Training system 1200 may perform the plurality of training iterations during such a training epoch. During a training iteration, generator model 1204 may generate, based on input data for the training iteration, an output design for the training iteration. For example, training system 1200 may inject randomized data into a latent space vector of generator model 1204. In some examples, the randomized data includes random noise. The output designs may be designs of baseplate elements, augmentation elements, fixation holes, complete prostheses, etc., as needed.

Training system 1200 may provide the output design generated by generator model 1204 to discriminator model 1206. Discriminator model 1206 may generate, based on the output design for the training iteration, a discriminator output for the training iteration. The discriminator output for the training iteration may comprise a first value indicating a level of confidence that generator model 1204 generated the output design for the training iteration and a second value indicating a level of confidence that generator model 1204 did not generate the output design for the training iteration. In training iterations, training system 1200 may provide the generated output designs and/or reference designs 1208 not generated by generator model 1204 to discriminator model 1206.

Training system 1200 may determine a loss value for the training iteration based on the discriminator output for the respective training iteration. Training system 1200 may update parameters of generator model 1204 and/or discriminator model 1206 based on the loss value for the respective training iteration. Training system 1200 may determine the loss value for the training iteration in one of a variety of ways. For instance, in an example where the discriminator output includes a first value indicating a level of confidence that the discriminator input (which may be the output design of generator model 1204 or a reference model design) for the training iteration was generated by generator model 1204 and a second value indicating a level of confidence that the discriminator input for the training iteration was not generated by generator model 1204, training system 1200 may calculate a cross-entropy loss value based on the first value, the second value, and a value indicating whether the output bone model actually represents a premorbid bone. If discriminator model 1206 correctly determined the discriminator input bone model was generated by generator model 1204, training system 1200 may use the cross-entropy loss value to perform backpropagation on each layer of discriminator model 1206 and each layer of generator model 1206. In other words, the backpropagation may proceed as though the layers of discriminator model 1206 were concatenated to the layers of generator model 1204. On the other hand, if discriminator model 1206 makes an incorrect determination (e.g., if discriminator model 1206 determines that the discriminator input was generated by generator model 1204 when the discriminator input was not generated by generator model 1204 or if discriminator model 1206 determines that the discriminator input was not generated by generator model 1204 when the discriminator input bone model was generated by generator model 1204), training system 1200 may use the cross-entropy loss value to perform backpropagation on each layer of discriminator model 1206 without changing weights of generator model 1204.

In general, when performing the backpropagation process, a loss value may be calculated, e.g., as discussed above. For each weight of each neuron of each layer of neurons of a neural network, a change value for the weight may be calculated based on the loss value. The error value can be seen as an output of a function taking as a parameter an n-dimensional array containing the weights of the neural network. A change value for a weight represents a step descending a gradient of the error function along a dimension associated with the weight. Thus, the change value for the weight may be equal to a partial derivative of the weight with respect to the loss value. An updated value of the weight may be determined by subtracting the change value, multiplied by a learning rate, from the weight. In some examples, initial training unit 302 may add Gaussian error values to the change values for weights of neurons that generate values included in latent space vector 714. The Gaussian error values are values that have a Gaussian distribution centered on 0. Addition of the Gaussian error values may promote a more stable training process.

In some examples, discriminator model 1206 outputs a single discriminator output that indicates a level of confidence that the discriminator input is a "real" discriminator input (i.e., a discriminator input not generated by generator model 1204). Thus, the discriminator output may be closer to 1 if discriminator model 1206 has greater confidence that the discriminator input is "real." The discriminator output may be closer to 0 if discriminator model 1206 is less confident that the discriminator input is "real." In other words, the discriminator output may be closer to 0 if discriminator model 1206 is more confident that the discriminator input is "fake" (i.e., that generator model 1204 generated the discriminator input bone model).

Training system 1200 may use a loss function based on binary cross-entropy to train GAN 1202 (i.e., to train generator model 1204 and discriminator model 1206). The general form of a binary cross-entropy loss function is represented below:

$$\mathcal{L} = -\sum y * \ln(\hat{y})) + (1 - y) * \ln(1 - \hat{y})$$

where $\mathcal{L}$ is a loss value, y is the ground truth (e.g., y is equal to 0 if the discriminator input was generated by premorbid reconstruction ML model 220 and y is equal to 1 if generator model 1204 did not generate the discriminator input bone model), $\hat{y}$ is the output of discriminator model 1206, and the summation is over each possible value of y (i.e., 0 and 1). When the discriminator input is "real," the output of discriminator model 1206 (i.e., $\hat{y}$) is D(x), where D is a function representing operation of discriminator model 1206 and x is the discriminator input. When the discriminator input is "fake," the output of discriminator model 1206 (i.e., $\hat{y}$) is D(G(z)), where G is a function representing operation of generator model 1204 and z is input to generator model 1204.

Thus, when the discriminator input is "fake," the loss function may be written as:

$$\mathcal{L} = y * \ln(D(G(z))) + (1 - y) * \ln(1 - D(G(z)))$$

Because discriminator model 1206 should output 0 when the discriminator input is "fake," the above equation may be simplified as:

$$\mathcal{L} = 0 * \ln(D(G(z))) + (1 - 0) * \ln(1 - D(G(z))) = \ln(1 - D(G(z)))$$

On the other hand, when the discriminator input is "real," the loss function may be written as:

$$\mathcal{L} = y * \ln(D(x)) + (1 - y) * \ln(1 - D(x))$$

Note that G is not in the equation above because generator model 1204 was not involved in the generation of the discriminator input. In the above equation, x is the discriminator input. Because discriminator model 1206 should output 1 when the discriminator input is "real," the above equation may be simplified as:

$$\mathcal{L} = 1 * \ln(D(x)) + (1 - 1) * \ln(1 - D(x)) = \mathcal{L} = \ln(D(x))$$

Thus, the loss function of GAN 1202 (i.e., generator model 1204 and discriminator model 1206) as a whole may be represented as:

$$\mathcal{L} = \ln(D(x)) + \ln(1 - D(G(z)))$$

It may be more efficient to train GAN 1202 using a backpropagation process that uses a loss value that is determined based on multiple inputs to GAN 1202 (i.e., inputs to decoder model 1106 of generator model 1204 and real premorbid bone models to discriminator model 1206) than a loss value that is determined based on a single input to GAN 1202. Thus, during a training epoch, GAN 1202 may provide multiple inputs to GAN 1202 and determine multiple loss values. GAN 1202 may then determine an expected value of the loss values. The expected value of the loss values may be a form of an average of the loss values. The expected value of the loss values may be the sum of the expected loss values for "real" discriminator inputs and the expected loss values for "fake" discriminator inputs. Thus, the loss value that training system 1200 may use for the backpropagation process (i.e., the expected loss value) may be represented as:

$$E(\mathcal{L}) = E(\ln(D(x))) + E(\ln(1 - D(G(z))))$$

Training system 1200 may train generator model 1204 and discriminator model 1206 in alternating periods. Each of the periods may include one or more training epoch. When training system 1200 is training discriminator model 1206, training system 1200 may provide multiple inputs to GAN 1202 (e.g., inputs to generator model 1204 and reference designs 1208 to discriminator model 1206). When the input to GAN 1202 is an input to generator model 1204, training system 1200 may perform forward propagation through generator model 1204 and discriminator model 1206. When the input to GAN 1202 is a reference design, training system 1200 performs forward propagation only through discriminator model 1206. In either case, training system 1200 may determine loss values for each input to GAN 1202 and use these loss values to determine an expected loss value, e.g., as shown in the equation above. For instance, if there are m inputs to GAN 1202, GAN training unit 300 may add together the loss values and divide the resulting sum by m. Training system 1200 may then use the expected loss value in a backpropagation process to update the weights of discriminator model 1206. The backpropagation process used to update the weights of discriminator model 1206 may use gradient ascent. The backpropagation process used to update the weights of discriminator model 1206 may be represented by the following equation:

$$\frac{\partial}{\partial \theta_d} \frac{1}{m} [\ln(D(x) + \ln(1 - D(G(z)))]$$

where $\theta_d$ is a weight of discriminator model 1206 and m is the number of inputs to GAN 1202. Training system 1200 does not update the weights of generator model 1204 during a training period for discriminator model 1206.

After completing a training period for discriminator model 1206, training system 1200 may initiate a training period for generator model 1204. When training system 1200 is training premorbid reconstruction ML model 220, training system 1200 may provide multiple inputs to decoder model 1106 of premorbid reconstruction ML model 220 and may perform forward propagation through decoder model 1106 of generator model 1204 and discriminator model 1206. Training system 1200 may determine loss values for each input to decoder model 1106 and use these loss values to determine an expected loss value. Training system 1200 may then use the expected loss value in a backpropagation process to update weights of generator model 1204. The backpropagation process used to update the weights of decoder model 1106 of generator model 1204 may use gradient descent, which may be represented by the following equation:

$$\frac{\partial}{\partial \theta_g} \frac{1}{m} [\ln(1 - D(G(z))]$$

where $\theta_g$ is a weight of generator model 1204 and m is the number of inputs to GAN 1202. Training system 1200 does not update weights of generator model 1204.

In some examples, initial design system 702 is based on the framework for exploring generative 3D shapes using autoencoder networks, e.g., as described in Umetani, "Exploring generative 3D shapes using autoencoder networks" (2017). In such examples, initial design system 702 may parameterize a 3D shape (e.g., a 3D shape of a baseplate, augmentation elements, complete prostheses, etc.), which may be represented using a triangle mesh, into a fixed-size vector that has a relatively high number of dimensions. Initial design system 702 may apply an autoencoder to the vector to obtain a feature vector that has a smaller number of dimensions that the initial fixed-size vector (e.g., 10 dimensions). The autoencoder may be a feed-forward neural network with four fully connected layers. An output layer of the autoencoder may have a linear activation function. Other layers of the autoencoder may use a sigmoid activation function. Initial design system 702 may explore designs by changing the input values q (i.e., modifying one or more elements of a latent space vector) to the decoder model of the autoencoder. In some examples, initial design system 702 is based on the framework described in Burnap et al., "Estimating and Exploring the Product Form Design Space Using Deep Generative Models," Proceedings of the ASME 2016 International Design Engineering Technical Conferences and Computers and Information in Engineering Conference, IDETC/CIE 2016, Aug. 21-24, 2016, Charlotte, North Carolina.

Figure 13:
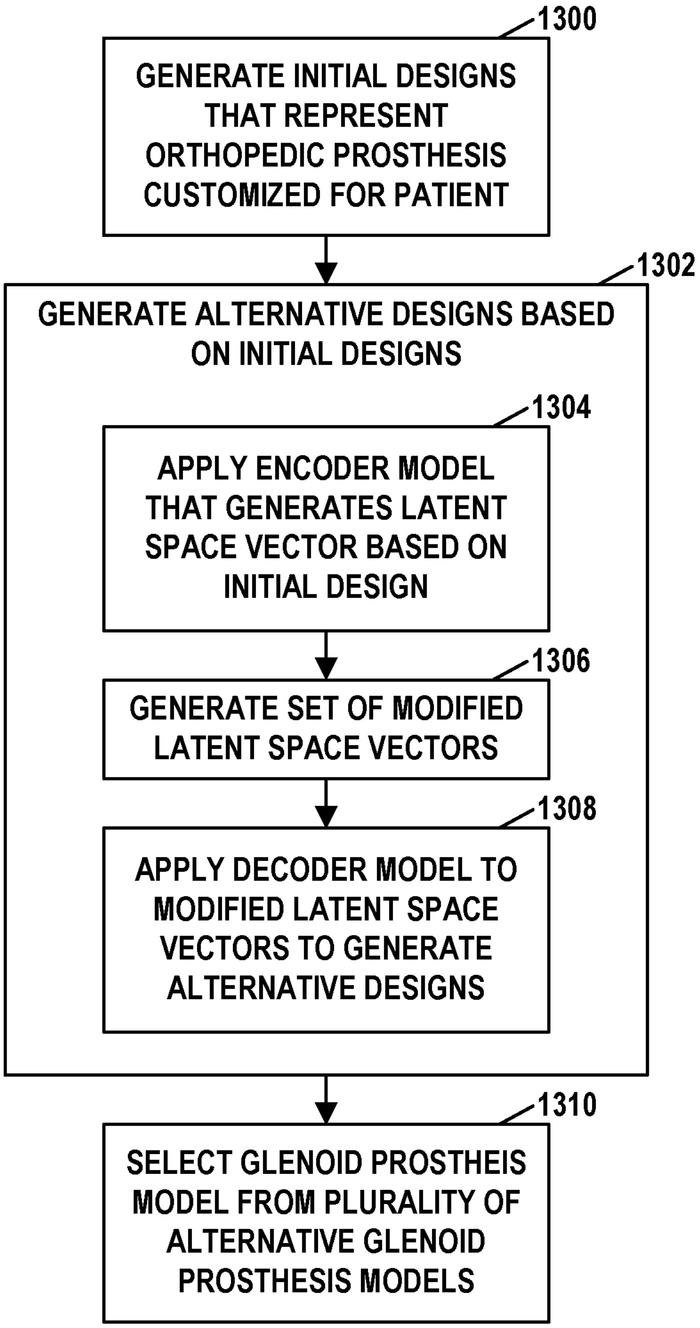
FIG. 13 is a flowchart illustrating an example operation of a planning system according to techniques of this disclosure.

FIG. 13 is a flowchart illustrating an example operation of a planning system 126 according to techniques of this disclosure. In the example of FIG. 13, initial design system 702 may generate a set of one or more initial designs that represents an orthopedic prosthesis customized for a patient (1300). As used in this disclosure, an "orthopedic prosthesis" may refer to a complete prosthesis or a component of a prosthesis. For instance, the orthopedic prosthesis may be or comprise baseplate element of a glenoid prosthesis. The baseplate element may have an extension that defines a fixation hole positioned for attaching the baseplate element to an acromion process or coracoid process of the patient. In some examples, prosthesis sizing system 204 may apply sizing model 222 that recommends a size of the baseplate element. In some examples, the orthopedic prosthesis is an augmentation element of a glenoid prosthesis.

As described elsewhere in this disclosure, initial design system 702 may perform a topology optimization process that generates one or more designs in the set of initial designs. The designs generated by the topology optimization process have topologies that comply with a set of one or more constraints based on patient data for the patient. In some examples, as part of generating the initial designs, initial design system 702 may train a generative model 908 based on the one or more designs generated by the topology optimization process and may apply generative model 908 to generate one or more additional designs in the set of initial designs. In some examples, initial design system 702 may use a GAN to train the generative model.

Additionally, design variation system 704 may generate one or more alternative designs based on the set of initial designs (1302). The one or more alternative designs represent the orthopedic prosthesis customized for the patient. As part of generating the one or more alterative designs, design variation system 704 may, for each initial design in the set of initial designs, apply encoder model 710 that generates a latent space vector 714 based on the initial design (1304). The encoder model is a first ML model and is part of an autoencoder. The latent space vector has reduced dimensionality relative to the initial design.

Furthermore, design variation system 704 may generate a set of one or more modified latent space vectors by modifying one or more elements of the latent space vector (1306). Design variation system 704 may apply a design of experiments (DOE) approach for modifying latent space vectors. For instance, design variation system 704 may systematically modify elements in the modified latent space vectors to determine which elements (and adjustment amounts) result in designs that satisfy one or more constraints. Design variation system 704 may assess whether a change in a single factor has in fact resulted in a change/improvement to the process as a whole, like in range of motion. Design variation system 704 may have a ranked list of important through unimportant factors (e.g., range of motion (ROM) and fixation most important to least important like version/inclination range) that affect the process. Thus, the idea is to define several factors within a range of variation and test each configuration to save some optimization time.

Design variation system 704 may apply decoder model 712 to the one or more modified latent space vectors to generate a set of one or more alternative designs (1308). Decoder model 712 is a second ML model and is part of the autoencoder. The alternative designs represent the orthopedic prosthesis.

Selection system 706 may select a design for the orthopedic prosthesis from the initial designs or the set of alternative designs (1310). In some examples, selection system 706 applies a cost function to the initial designs and alternative designs to generate cost values for the alternative glenoid prosthesis models. Selection system 706 may select the design comprises selecting the design based on the cost values for the initial designs and alternative designs. In some examples, the cost function is based on at least one of: amounts of bone removal associated with the alternative designs (e.g., alternative glenoid prosthesis models), or reference plane levels of the alternative designs (e.g., alternative glenoid prosthesis models).

Planning system 126 may perform the operation of FIG. 13 in response to various events. For example, profile customization system 206 of planning system 126 may output a user interface (e.g., user interface 500) for display. The user interface may indicate a profile of the baseplate element. Profile customization system 206 may receive an indication of user input to modify the profile of the baseplate element. In this example, planning system 126 may generate the initial designs, generates the alternative designs, and selects the design based on the modified profile of the baseplate element. For instance, during topology constraint optimization, the initial designs may be constrained to the modified profile. In some examples, selection system 706 may select a design based at least on conformity to the modified profile of the baseplate element. In some examples, the user interface may further indicate a position of a fixation hole defined in the baseplate element. The indication of user input to modify the profile of the baseplate element may comprise an indication of user input to move the fixation hole to a position outside the profile of the baseplate element.

In some examples, case classification system 200 applies one or more case classification models (e.g., current case classification model 602) to patient data for the patient to determine a classification of the orthopedic prosthesis from among a plurality of orthopedic prosthesis classifications. The plurality of orthopedic prosthesis classifications may include patient-matched glenoid prostheses, patient-specific glenoid prostheses, glenoid prostheses customized for patients, or patient-tailored glenoid prostheses. Planning system 126 may generate the set of initial designs, generate the alternative designs, and select the design in response to determining that the classification of the orthopedic prosthesis is the glenoid prostheses customized for patients. In such examples, the patient data may include a bone model of the patient. In some examples, the patient data for the patient further includes one or more of: an age of the patient, a sex of the patient, and activity expectations of the patient. The case classification model may be one of a voxel-based ML model, a point cloud-based ML model, a view-based ML model, or a mesh data-based ML model.

In some examples, premorbid modeling system 202 may generate a premorbid bone model of a scapula of the patient. Additionally, premorbid modeling system 202 may determine a joint line or reference plane of a glenoid fossa of the scapula of the patient. In some examples, planning system 126 generates the set of initial designs based on the joint line or reference plane of the glenoid fossa. In some examples, planning system 126 selects the design based on the joint line or reference plane of the glenoid fossa. For instance, a cost function used by selection system 706 may penalize designs based on their deviation from the joint line or reference plane.

The following is a non-limiting list of clauses describing examples of this disclosure.

Clause 1. A method comprising: generating, by a computing system, a set of one or more initial designs that represents an orthopedic prosthesis customized for a patient; generating, by the computing system, one or more alternative designs based on the set of initial designs, wherein the one or more alternative designs represent the orthopedic prosthesis customized for the patient, and wherein generating the one or more alterative designs comprises, for each initial design in the set of initial designs: applying, by the computing system, an encoder model that generates a latent space vector based on the initial design, wherein the encoder model is a first machine learning (ML) model, the encoder model is part of an autoencoder, and the latent space vector has reduced dimensionality relative to the initial design; generating, by the computing system, a set of one or more modified latent space vectors by modifying one or more elements of the latent space vector; applying, by the computing system, a decoder model to the one or more modified latent space vectors to generate one or more of the alternative designs, wherein the decoder model is a second ML model, the decoder model is part of the autoencoder; and selecting, by the computing system, a design for the orthopedic prosthesis from the initial designs or the set of alternative designs.

Clause 2. The method of clause 1, wherein generating the set of one or more initial design comprises performing, by the computing system, a topology optimization process that generates one or more designs in the set of one or more initial designs, wherein the designs generated by the topology optimization process have topologies that comply with a set of one or more constraints based on patient data for the patient.

Clause 3. The method of clause 2, further comprising: training, by the computing system, a generative model based on the one or more designs generated by the topology optimization process, wherein the generative model is a third ML model; and applying, by the computing system, the generative model to generate one or more additional designs in the set of initial designs.

Clause 4. The method of clause 3, wherein training the generative model comprises using a generative adversarial model (GAN) to train the generative model.

Clause 5. The method of any of clauses 1-4, wherein the orthopedic prosthesis comprises a baseplate element of a glenoid prosthesis, the baseplate element having an extension that defines a fixation hole positioned for attaching the baseplate element to an acromion process or coracoid process of the patient.

Clause 6. The method of clause 5, further comprising applying, by the computing system, a sizing model that recommends a size of the baseplate element, wherein the sizing model is a third ML model.

Clause 7. The method of any of clauses 5-6, wherein: the method further comprises: outputting, by the computing system, a user interface for display, the user interface indicating a profile of the baseplate element; and receiving, by the computing system, an indication of user input to modify the profile of the baseplate element, and the computing system generates the initial designs, generates the alternative designs, and selects the design based on the modified profile of the baseplate element.

Clause 8. The method of clause 7, wherein: the user interface further indicates a position of a fixation hole defined in the baseplate element, and the indication of user input to modify the profile of the baseplate element comprises an indication of user input to move the fixation hole to a position outside the profile of the baseplate element.

Clause 9. The method of any of clauses 1-4, wherein the orthopedic prosthesis is an augmentation element of a glenoid prosthesis.

Clause 10. The method of any of clauses 1-9, wherein: the method further comprises applying, by the computing system, a case classification model to patient data for the patient to determine a classification of the orthopedic prosthesis from among a plurality of orthopedic prosthesis classifications, wherein the case classification model is a third ML model and the plurality of orthopedic prosthesis classifications includes patient-matched glenoid prostheses, patient-specific glenoid prostheses, and glenoid prostheses customized for patients, and the computing system generates the set of initial designs, generates the alternative designs, and selects the design in response to determining that the classification of the orthopedic prosthesis is the glenoid prostheses customized for patients.

Clause 11. The method of clause 10, wherein the patient data for the patient includes a bone model of the patient.

Clause 12. The method of clause 11, wherein the case classification model is one of: a voxel-based ML model, a point cloud-based ML model, a view-based ML model, or a mesh data-based ML model.

Clause 13. The method of any of clauses 10-12, wherein the patient data for the patient further includes one or more of: an age of the patient, a sex of the patient, and activity expectations of the patient.

Clause 14. The method of any of clauses 1-13, further comprising: generating, by the computing system, a premorbid bone model of a scapula of the patient; and determining, by the computing system, a joint line or reference plane of a glenoid fossa of the scapula of the patient in the premorbid bone model of the scapula, and wherein at least one of: generating the set of initial designs comprises generating, by the computing system, the set of initial designs based on the joint line or reference plane of the glenoid fossa, or selecting the design comprises selecting, by the computing system, the design based on the joint line or reference plane of the glenoid fossa.

Clause 15. The method of any of clauses 1-14, wherein selecting the design comprises: applying, by the computing system, a cost function to the initial designs and alternative designs to generate cost values for the initial designs and alternative designs; and selecting the design comprises selecting, by the computing system, the design based on the cost values for the initial designs and alternative designs.

Clause 16. The method of clause 15, wherein the cost function is based on at least one of: amounts of bone removal associated with the alternative glenoid prosthesis models, or reference plane levels of the alternative glenoid prosthesis models.

Clause 17. A computing system comprising: a storage system; and processing circuitry configured to perform the methods of any of clauses 1-16.

Clause 18. A non-transitory computer readable storage medium having instructions stored thereon that, when executed, cause a computing system to perform the methods of any of clauses 1-16.

While the techniques been disclosed with respect to a limited number of examples, those skilled in the art, having the benefit of this disclosure, will appreciate numerous modifications and variations there from. For instance, it is contemplated that any reasonable combination of the described examples may be performed. It is intended that the appended claims cover such modifications and variations as fall within the true spirit and scope of the invention.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Operations described in this disclosure may be performed by one or more processors, which may be implemented as fixed-function processing circuits, programmable circuits, or combinations thereof, such as one or more digital signal processors (DSPs), general purpose microprocessors, application specific integrated circuits (ASICs), field programmable gate arrays (FPGAs), or other equivalent integrated or discrete logic circuitry. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute instructions specified by software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. Accordingly, the terms "processor" and "processing circuitry," as used herein may refer to any of the foregoing structures or any other structure suitable for implementation of the techniques described herein.

Various examples have been described. These and other examples are within the scope of the following claims.

The invention claimed is:

1. A method comprising:

generating, by a computing system, a set of one or more initial designs that represents an orthopedic prosthesis customized for a patient;

generating, by the computing system, one or more alternative designs based on the set of one or more initial designs, wherein the one or more alternative designs represent the orthopedic prosthesis customized for the patient, and wherein generating the one or more alternative designs comprises, for each initial design in the set of one or more initial designs:

applying, by the computing system, an encoder model that generates a latent space vector based on the initial design, wherein the encoder model is a first machine learning (ML) model, the encoder model is part of an autoencoder, and the latent space vector has reduced dimensionality relative to the initial design;

generating, by the computing system, a set of one or more modified latent space vectors by modifying one or more elements of the latent space vector; and applying, by the computing system, a decoder model to the one or more modified latent space vectors to generate one or more of the alternative designs, wherein the decoder model is a second ML model, the decoder model is part of the autoencoder; and selecting, by the computing system, a design for the orthopedic prosthesis from the set of one or more initial designs or the one or more alternative designs.

2. The method of claim 1, wherein generating the set of one or more initial designs comprises performing, by the computing system, a topology optimization process that generates one or more designs in the set of one or more initial designs, wherein the designs generated by the topology optimization process have topologies that comply with a set of one or more constraints based on patient data for the patient.

3. The method of claim 2, further comprising:

training, by the computing system, a generative model based on the one or more designs generated by the topology optimization process, wherein the generative model is a third ML model; and applying, by the computing system, the generative model to generate one or more additional designs in the set of one or more initial designs.

4. The method of claim 3, wherein training the generative model comprises using a generative adversarial model (GAN) to train the generative model.

5. The method of claim 1, wherein the orthopedic prosthesis comprises a baseplate element of a glenoid prosthesis, the baseplate element having an extension that defines a fixation hole positioned for attaching the baseplate element to an acromion process or coracoid process of the patient.

6. The method of claim 5, further comprising applying, by the computing system, a sizing model that recommends a size of the baseplate element, wherein the sizing model is a third ML model.

7. The method of claim 5, wherein:

the method further comprises:

outputting, by the computing system, a user interface for display, the user interface indicating a profile of the baseplate element; and receiving, by the computing system, an indication of user input to modify the profile of the baseplate element to generate a modified profile of the baseplate element, and the computing system generates the set of one or more initial designs, generates the one or more alternative designs, and selects the design for the orthopedic prosthesis based on the modified profile of the baseplate element.

8. The method of claim 7, wherein:

the user interface further indicates a position of a fixation hole defined in the baseplate element, and the indication of user input to modify the profile of the baseplate element comprises an indication of user input to move the fixation hole to a position outside the profile of the baseplate element.

9. The method of claim 1, wherein the orthopedic prosthesis is an augmentation element of a glenoid prosthesis.

10. The method of claim 1, wherein:

the method further comprises applying, by the computing system, a case classification model to patient data for the patient to determine a classification of the orthopedic prosthesis from among a plurality of orthopedic prosthesis classifications, wherein the case classification model is a third ML model and the plurality of orthopedic prosthesis classifications includes patient-matched glenoid prostheses, patient-specific glenoid prostheses, and glenoid prostheses customized for patients, and the computing system generates the set of one or more initial designs, generates the one or more alternative designs, and selects the design in response to determining that the classification of the orthopedic prosthesis is a glenoid prostheses customized for patients.

11. The method of claim 10, wherein the patient data for the patient includes a bone model of the patient.

12. The method of claim 11, wherein the case classification model is one of:

a voxel-based ML model, a point cloud-based ML model, a view-based ML model, or a mesh data-based ML model.

13. The method of claim 10, wherein the patient data for the patient further includes one or more of: an age of the patient, a sex of the patient, and activity expectations of the patient.

14. The method of claim 1, further comprising:

generating, by the computing system, a premorbid bone model of a scapula of the patient; and determining, by the computing system, a joint line or reference plane of a glenoid fossa of the scapula of the patient in the premorbid bone model of the scapula, and wherein at least one of:

generating the set of one or more initial designs comprises generating, by the computing system, the set of one or more initial designs based on the joint line or reference plane of the glenoid fossa, or selecting the design comprises selecting, by the computing system, the design based on the joint line or reference plane of the glenoid fossa.

15. The method of claim 1, wherein selecting the design comprises:

applying, by the computing system, a cost function to the one or more initial designs and the one or more alternative designs to generate cost values for the set of one or more initial designs and the one or more alternative designs; and selecting the design comprises selecting, by the computing system, the design for the orthopedic prosthesis based on the cost values for the set of one or more initial designs and the one or more alternative designs.

16. The method of claim 15, wherein the cost function is based on at least one of:

amounts of bone removal associated with the one or more alternative designs, or reference plane levels of the one or more alternative designs.

17. A computing system comprising:

a storage system; and processing circuitry configured to:

generate a set of one or more initial designs that represents an orthopedic prosthesis customized for a patient;

generate one or more alternative designs based on the set of one or more initial designs, wherein the one or more alternative designs represent the orthopedic prosthesis customized for the patient, and wherein processing circuitry is configured to, as part of generating the one or more alternative designs, for each initial design in the set of one or more initial designs:

apply an encoder model that generates a latent space vector based on the initial design, wherein the encoder model is a first machine learning (ML) model, the encoder model is part of an autoencoder, and the latent space vector has reduced dimensionality relative to the initial design;

generate a set of one or more modified latent space vectors by modifying one or more elements of the latent space vector; and apply a decoder model to the one or more modified latent space vectors to generate one or more of the alternative designs, wherein the decoder model is a second ML model, the decoder model is part of the autoencoder; and select a design for the orthopedic prosthesis from the set of one or more initial designs or the one or more alternative designs.

18. The computing system of claim 17, wherein the processing circuitry is configured to, as part of generating the set of one or more initial designs, perform a topology optimization process that generates one or more designs in the set of one or more initial designs, wherein the designs generated by the topology optimization process have topologies that comply with a set of one or more constraints based on patient data for the patient.

19. The computing system of claim 17, wherein the orthopedic prosthesis comprises one of:

a baseplate element of a glenoid prosthesis, the baseplate element having an extension that defines a fixation hole positioned for attaching the baseplate element to an acromion process or coracoid process of the patient, or an augmentation element of the glenoid prosthesis.

20. A non-transitory computer readable storage medium having instructions stored thereon that, when executed, cause a computing system to generate a set of one or more initial designs that represents an orthopedic prosthesis customized for a patient;

generate one or more alternative designs based on the set of one or more initial designs, wherein the one or more alternative designs represent the orthopedic prosthesis customized for the patient, and wherein processing circuitry is configured to, as part of generating the one or more alternative designs, for each initial design in the set of one or more initial designs:

apply an encoder model that generates a latent space vector based on the initial design, wherein the encoder model is a first machine learning (ML) model, the encoder model is part of an autoencoder, and the latent space vector has reduced dimensionality relative to the initial design;

generate a set of one or more modified latent space vectors by modifying one or more elements of the latent space vector; and apply a decoder model to the one or more modified latent space vectors to generate one or more of the alternative designs, wherein the decoder model is a second ML model, the decoder model is part of the autoencoder; and select a design for the orthopedic prosthesis from the set of one or more initial designs or the one or more alternative designs.

* * * * *